US009609888B2

(12) United States Patent
Berg et al.

(10) Patent No.: US 9,609,888 B2
(45) Date of Patent: Apr. 4, 2017

(54) NUTRITIONAL COMPOSITIONS CONTAINING SYNERGISTIC COMBINATION AND USES THEREOF

(71) Applicant: Mead Johnson Nutrition Company, Glenview, IL (US)

(72) Inventors: Brian Berg, Evansville, IN (US); Zeina Jouni, Evansville, IN (US); Anja Wittke, Evansville, IN (US); Rosaline Waworuntu, Evansville, IN (US); Maciej Chichlowski, Fair Oaks, CA (US)

(73) Assignee: Mead Johnson Nutrition Company, Glenview, IL (US)

( * ) Notice: Subject to any disclaimer, the term of this patent is extended or adjusted under 35 U.S.C. 154(b) by 89 days.

(21) Appl. No.: 13/955,492

(22) Filed: Jul. 31, 2013

(65) Prior Publication Data

US 2015/0037455 A1    Feb. 5, 2015

(51) Int. Cl.

| A23L 1/29 | (2006.01) |
|---|---|
| A23L 1/305 | (2006.01) |
| A23L 1/30 | (2006.01) |
| A61K 38/40 | (2006.01) |
| A61K 31/702 | (2006.01) |
| A61K 35/20 | (2006.01) |
| A61K 31/202 | (2006.01) |
| A61K 31/685 | (2006.01) |
| A61K 31/7032 | (2006.01) |
| A61K 38/01 | (2006.01) |
| A23L 33/00 | (2016.01) |
| A23L 33/115 | (2016.01) |
| A23L 33/12 | (2016.01) |
| A23L 33/17 | (2016.01) |
| A23L 33/21 | (2016.01) |
| A23L 33/26 | (2016.01) |

(52) U.S. Cl.
CPC ............. *A23L 1/296* (2013.01); *A23L 33/115* (2016.08); *A23L 33/12* (2016.08); *A23L 33/17* (2016.08); *A23L 33/21* (2016.08); *A23L 33/26* (2016.08); *A23L 33/40* (2016.08); *A61K 31/202* (2013.01); *A61K 31/685* (2013.01); *A61K 31/702* (2013.01); *A61K 31/7032* (2013.01); *A61K 35/20* (2013.01); *A61K 38/018* (2013.01); *A61K 38/40* (2013.01)

(58) Field of Classification Search
None
See application file for complete search history.

(56) References Cited

U.S. PATENT DOCUMENTS

| 4,791,193 A | 12/1988 | Okonogi et al. |
|---|---|---|
| 5,374,567 A | 12/1994 | Cartagena |
| 5,397,591 A | 3/1995 | Kyle |
| 5,550,156 A | 8/1996 | Kyle |
| 5,591,479 A | 1/1997 | Ponroy |
| 5,686,491 A | 11/1997 | Sherwood |
| 5,709,888 A | 1/1998 | Gil et al. |
| 5,849,885 A | 12/1998 | Nuyens |
| 5,861,491 A | 1/1999 | Nuijens |
| 5,919,913 A | 7/1999 | Nuyens |
| 6,620,326 B1 | 9/2003 | Lihme |
| 6,977,046 B2 | 12/2005 | Hubbuch |
| 7,354,896 B2 | 4/2008 | Kirwin et al. |
| 7,368,141 B2 | 5/2008 | Lihme |
| 7,812,138 B2 | 10/2010 | Lihme |
| 7,851,450 B2 | 12/2010 | Beerman et al. |
| 8,445,053 B2 | 5/2013 | Holst et al. |
| 2008/0003329 A1 | 1/2008 | Rueda et al. |
| 2008/0003330 A1 | 1/2008 | Rueda et al. |
| 2010/0104696 A1* | 4/2010 | Banavara ............... A23L 1/296 426/72 |
| 2011/0009349 A1 | 1/2011 | Hodgkinson et al. |
| 2011/0293784 A1 | 12/2011 | Wittke |
| 2012/0269929 A1 | 10/2012 | Lippman et al. |
| 2012/0276057 A1 | 11/2012 | Steenhout et al. |
| 2013/0071446 A1 | 3/2013 | Van Der Beek et al. |

(Continued)

FOREIGN PATENT DOCUMENTS

| CN | 101316521 A | 12/2008 |
|---|---|---|
| CN | 101370395 A | 2/2009 |

(Continued)

OTHER PUBLICATIONS

Mintel, "Golden Growing-Up Formula Goat Milk Powder," Database Accession No. 1694223, Jan. 2012 XP002730875.
Mintel, "Growing-Up Milk Powder (Stage 3) with Lactoferrin," Database Accession No. 2081489, Jan. 2012 XP002730876.
Mintel, "Growing-Up Milk for Children," Database Accession No. 2085763, Jun. 2013 XP002730877.
Mintel, "New Birth Formula," Database Accession No. 1249000, Jan. 2010 XP002673470.
Mintel, "Stage 2 Infant Formula," Database Accession No. 2032623, Mar. 2013 XP002730874.
Awad, K., et al., "Effects of exercise and nutritional intake on sleep architecture in adolescents," Sleep Breath. Mar. 2013; 17(1): 117-124.

(Continued)

*Primary Examiner* — Amber D Steele
*Assistant Examiner* — Schulyer Milton
(74) *Attorney, Agent, or Firm* — OspreyIP, PLLC; James R. Cartiglia; Bethany J. Whelan

(57) ABSTRACT

A composition and method for enhancing brain development in a pediatric subject, the method including administering to the pediatric subject a nutritional composition having up to about 7 g/100 kcal of a fat or lipid source, wherein the fat or lipid source includes at least about 0.5 mg/100 kcal of milk or non-milk polar lipids; up to about 5 g/100 kcal of a protein source; at least about 15 mg/100 kcal of lactoferrin from a non-human source; about 0.015 g/100 kcal to about 0.15 g/100 kcal of a prebiotic composition including polydextrose and/or galactooligosaccharide; and at least about 5 mg/100 kcal of a source of long chain polyunsaturated fatty acids.

20 Claims, 7 Drawing Sheets

(56) References Cited

U.S. PATENT DOCUMENTS

| | | | |
|---|---|---|---|
| 2013/0150306 A1 | 6/2013 | Wittke | |
| 2014/0161928 A1* | 6/2014 | Hageman | A23L 1/296 426/2 |
| 2014/0199265 A1 | 7/2014 | Kuang et al. | |
| 2015/0037455 A1 | 2/2015 | Chichlowski et al. | |

FOREIGN PATENT DOCUMENTS

| | | |
|---|---|---|
| CN | 102215702 A | 10/2011 |
| EP | 0183572 | 7/1992 |
| EP | 0484266 | 7/1992 |
| EP | 0433113 | 5/1995 |
| EP | 2046149 | 11/2010 |
| EP | 2251030 | 11/2010 |
| EP | 2251031 | 11/2010 |
| EP | 2258216 | 12/2010 |
| EP | 2258217 | 12/2010 |
| EP | 2258218 | 12/2010 |
| EP | 2594282 | 5/2013 |
| EP | 2638810 | 9/2013 |
| JP | H09172962 A | 7/1997 |
| WO | 9200799 | 1/1992 |
| WO | 9717132 | 5/1997 |
| WO | 2005051091 | 6/2005 |
| WO | 2011069987 | 6/2011 |
| WO | 2011115476 | 9/2011 |

OTHER PUBLICATIONS

Bemiller, J., "An Introduction to Pectins: Structure and Properties," Chemistry and Function of Pectins; Chapter 1; 1986.

Brenna, J., "Efficiency of conversion of a-linolenic acid to long chain n-3 fatty acids in man," Current Opinion in Clinical Nutrition and Metabolic Care 2002, 5:127-132.

Fanaro et al., "Acidic Oligosaccharides from Pectin Hydrolysate as New Component for Infant Formulae: Effect on Intestinal Flora, Stool Characteristics, and pH", Journal of Pediatric Gastroenterology and Nutrition, 41: 186-190, Aug. 2005.

Fenzl, T., et al., "Sleep disturbances in highly stress reactive mice: Modeling endophenotypes of major depression," BMC Neuroscience 2011, 12:29.

Gurnida, D., et al., "Association of complex lipids containing gangliosides with cognitive development of 6-month-old infants," Early Human Development (2012).

Herlenius, E., et al., "Development of neurotransmitter systems during critical periods," Experimental Neurology 190 (2004) S8-S21.

Kamemori, N., et al., "Trans-Endothelial and Trans-Epithelial Transfer of Lactoferrin in the Brain through BBB and BCSFB in Adult Rats," J. Vet. Med. Sci. 70(3): 313-315, 2008.

Kuhara, T., et al., "Oral Administration of Lactoferrin Increases NK Cell Activity in Mice via Increased Production of IL-18 and Type I IFN in the Small Intestine," Journal of Interferon & Cytokine Research 26:489-499 (2006).

Kunz, et al., Oligosaccharides in Human Milk: Structure, Functional, and Metabolic Aspects, Ann. Rev. Nutr. 20: 699-722 (2000).

Ling, J., et al.. "Perspectives on Interactions Between Lactoferrin and Bacteria," Biochemistry and Cell Biology, pp. 275-281 (2006).

Martinez, M., "Tissue levels of polyunsaturated fatty acids during early human development," J. Pediatr 1992;120: S129-38.

Martinez, M., et al., "Fatty Acid Composition of Human Brain Phospholipids During Normal Development," J. Neurochem. 71, 2528-2533 (1998).

McJarrow, P., et al., "Influence of dietary gangliosides on neonatal brain development," Nutrition Reviews vol. 67 (8):451-463.

Monaco, M., et al., "Addition of Polydextrose and Galactooligosaccharide to Formula Does Not Affect Bacterial Translocation in the Neonatal Piglet," JPGN 2011;52: 2010-216.

Morgan, B. L., et al., "Effects of environmental stimulation on brain N-acetylneuraminic acid content and behavior." J Nutr 110(3): 425-432, 1980.

Morgan, B., et al., "Effects of Administration of N-Acetylneuraminic Acid (NANA) on Brain NANA Content and Behavior," J. Nutr. 110: 416-424, 1980.

Mulder, A., et al., "Bovine lactoferrin supplementation supports immune and antioxidant status in healthy human males," Nutrition Research 28 (2008) 583-589.

Ochoa, T., et al., "Impact of Lactoferrin Supplementation on Growth and Prevalence of Giardia Colonization in Children," Brief Report CID 2008:46 (Jun. 15).

Rahman, M.D., M. et al., "Growth promotion and cell binding ability of bovine lactoferrin to Bifidobacterium longum," Anaerobe, 15(4): 133-137.

Ribeiro, T., et al., "Stool Pattern Changes in Toddlers Consuming a Follow-on Formula Supplemented With Polydextrose and Galactooligosaccharides," JPGN 2012;54: 288-290.

Salvini, F., et al., "A Specific Prebiotic Mixture Added to Starting Infant Formula Has Long-Lasting Bifidogenic Effects1-3," J. Nutr. 141: 1335-1339, 2011.

Savino, F., et al., "Lactobacillus reuteri DSM 17 938 in Infantile Colic: A Randomized, Double-Blind, Placebo-Controlled Trial," Pediatrics published online Aug. 16, 2010; DOI 10.1542/peds.2010-0433.

Scalabrin, D., et al., "New Prebiotic Blend of Polydextrose and Galacto-oligosaccharides Has a Bifidogenic Effect in Young Infants," JPGN 2012;54: 343-352.

Svennerholm, L., et al., "Chromatographic Separation of Human Brain Gangliosides," Journal of Neurochemistry, 1963, vol. 10, pp. 613-623.

Thomas, C., et al., "Histamine Derived from Probiotic Lactobacillus reuteri Suppresses TNF via Modulation of PKA and ERK Signaling," PLoS ONE 7(2):2012.

Veereman-Wauters, G., et al., "Milk fat globule membrane (INPULSE) enriched formula milk decreases febrile episodes and may improve behavioral regulation in young children," Nutrition 28 (2012) 749-752.

Veereman-Wauters, G., et al., "Physiological and Bifidogenic Effects of Prebiotic Supplements in Infant Formulai," JPGN 2011;52: 763-771.

Yadomae, T., "Structure and biological activities of fungal beta-1,3-glucans." Yakugaku Zasshi. 2000;120:413-431.

Ziegler, E., et al., "Term Infants Fed Formula Supplemented With Selected Blends of Prebiotics Grow Normally and Have Soft Stools Similar to Those Reported for Breast-fed Infants," Journal of Pediatric Gastroenterology and Nutrition 44:359-364 (2007).

Menard, O., et al., "Buffalo vs. cow milk fat globules: Size distribution, zeta-potential, compositions in total fatty acids and in polar lipids from the milk fat globule membrane," Food Chemistry 120 (2010) 544-551.

Ibfan "Breastfeeding and Brain Development (Cognitive Development)", Information Sheet-9, IBFAN Asia Pacific/Breastfeeding Promotion Network of India (BPNI), Feb. 2005, p. 1-2.

Armand, M., et al., "Effect of Human Milk or Formula on Gastric Function and Fat Digestion in the Premature Infant," Pediatric Research (1996) 40, 429-437.

Huang, M., et al., "Comparison of Lipid in Milk and Breast Milk," China Dairy Industry, vol. 19, No. 4, Aug. 29, 1991.

Michalski, M.C., et al., "Size Distribution of Fat Globules in Human Colostrum, Breast Milk, and Infant Formula," Journal of Dairy Science, vol. 88, No. 6, Dec. 31, 2005.

\* cited by examiner

| | C | G+P |
|---|---|---|
| Lactobacillus.delbrueckii | 0.3 | 0.5 |
| Lactobacillus.mucosae | 0.4 | 0.5 |
| Lactobacillus.johnsonii | 0.3 | 0.6 |
| Lactobacillus.reuteri | 0.1 | 0.6 |
| Lactobacillus.vaginalis | 0.1 | 0.6 |
| Lactobacillus.agilis | 0.1 | 0.2 |
| Lactobacillus.salivarius | 0.0 | 0.2 |
| Lactobacillus.gasseri | 0.1 | 0.2 |
| Lactobacillus.pointis | 0.1 | 0.1 |
| Lactobacillus.curvatus | 0.1 | 0.3 |
| Lactobacillus.pentosus | 0.2 | 0.0 |
| Lactobacillus.plantarum | 0.7 | 0.0 |
| Lactobacillus.amylovorus | 0.5 | 0.0 |
| Lactobacillus.sp | 0.5 | 0.2 |

*FIG. 1A*

| | C | G+P |
|---|---|---|
| Lactobacillus.rogosae | 0.1 | 0.0 |
| Lactobacillus.vaginalis | 0.2 | 0.0 |
| Lactobacillus.agilis | 0.0 | 0.2 |
| Lactobacillus.reuteri | 0.0 | 0.2 |
| Lactobacillus.sp | 0.0 | 0.2 |
| Lactobacillus.johnsonii | 0.1 | 0.8 |
| Lactobacillus.mucosae | 0.1 | 0.7 |

*FIG. 1B*

NUTRITIONAL COMPOSITIONS CONTAINING SYNERGISTIC COMBINATION AND USES THEREOF

TECHNICAL FIELD

The present disclosure relates generally to based nutritional compositions that are suitable for administration to pediatric subjects. More particularly, the disclosure relates to methods of supporting and promoting gastrointestinal health, cognitive development and brain function, and a method of reducing psychological stress in a pediatric subject via administration of the nutritional composition of the present disclosure. In some embodiments, the nutritional composition comprises certain classes of polar lipids, a prebiotic blend which includes polydextrose and galacto-oligosaccharides, lactoferrin, and a source of long chain polyunsaturated fatty acids, wherein the foregoing components may exhibit additive and/or synergistic beneficial effects.

BACKGROUND ART

Polar lipids, especially those found in milk, are composed of three major groups of lipids:
  (i) Glycerophospholipids such as phosphatidylcholine (PC), phosphatidylethanolamine (PE), phosphatidylserine (PS), and phosphatidylinositol (PI), and their derivatives.
  (ii) Sphingoids or sphingolipids such as sphingomyelin (SM) and glycosphingolipids comprise of cerebrosides (neutral glycosphingolipids containing uncharged sugars) and the gangliosides (GG, acidic glycosphingolipids containing sialic acid) and their derivatives.
  (iii) Cholesterol and its derivatives.

Polar lipids are constituent components of some foods, although their quality and quantity vary considerably depending on the food source. Dairy products such as milk and eggs are the richest sources of these polar lipids; the glycerophospholipids are also present in plants such as soybean. However, a child may need to consume a large amount of bovine milk (~2,000 ml) to obtain a reasonable amount of polar lipids. In addition, consumption of eggs is also limited in infants and children due to the possibility of the allergenic protein properties of eggs. Plants are not a source of some of the polar lipids and in particular gangliosides because they are unable to synthesize sialic acid, a component of gangliosides. Furthermore the quality of polar lipids in plants is totally different than milk polar lipids not only due to the fatty acid profile but also due to the ratio of the individual phospholipid components of these lipids.

Lactoferrin, an iron-binding glycoprotein, is one of the major multifunctional agents present in human milk. It has the capacity to bind two molecules of iron in a reversible fashion and can facilitate the uptake of iron within the intestines. Further, lactoferrin has been shown to be both bacteriostatic and bactericidal, and it aids in preventing intestinal infections in humans, especially in pediatric subjects. Additionally, human lactoferrin appears to have a positive effect on the symptoms of diarrheal diseases.

Moreover, the infant gut microflora is rapidly established in the first few weeks following birth, and it has a great impact on an infant's immune system. The nature of this intestinal colonization is initially determined by early exposure to environmental sources of microbes and by the general state of health of the infant. Whether the infant is breast-fed or formula-fed also has a strong influence on the intestinal bacterial population.

Human milk contains a number of factors that may contribute to the growth and population of the gut microflora of infants. Among these factors is a complex mixture of more than 130 different oligosaccharides that reach levels as high as 8-12 g/L in transitional and mature milk. Kunz, et al., *Oligosaccharides in Human Milk: Structure, Functional, and Metabolic Aspects*, Ann. Rev. Nutr. 20: 699-722 (2000). These oligosaccharides are resistant to enzymatic digestion in the upper gastrointestinal tract and reach the colon intact, where they then serve as substrates for colonic fermentation.

Cow's milk and many commercially available infant formulas that are based on cow's milk provide only trace amounts of oligosaccharides; as a result, prebiotics may be used to supplement the diet of formula-fed infants. Prebiotics have been defined as non-digestible food ingredients that beneficially affect the host by selectively stimulating the growth and/or activity of one or a limited number of cells in the gastrointestinal (GI) tract that can improve the health of the host.

Both the interaction among dietary components and among the microflora of the intestinal ecosystem are very complex. Consequently, then, the matrix of an infant formula or other pediatric nutritional composition may influence the effectiveness of prebiotics when such ingredients are provided as supplements in the diet of a formula-fed infant. Further, the type and concentration of lipids and proteins used in a formula matrix may also modulate the intestinal microbiota. Because human milk is the preferred source of infant nutrition, it is desirable to provide a formula matrix that mimics the qualities of human milk by allowing for effective supplementation of prebiotics as functional food ingredients.

Recently, it has been found that combining polar lipids with prebiotics, especially polydextrose (PDX) and galacto-oligosaccharides (GOS), lactoferrin, and long-chain polyunsaturated fatty acids (LCPUFAs) can lead to certain unique benefits. Accordingly, it would be beneficial to provide a nutritional composition for pediatric subjects that contains such a combination.

BRIEF SUMMARY

Briefly, the present disclosure is directed, in an embodiment, to a method for supporting and promoting gastrointestinal health, cognitive development and brain function, and modulating psychological stress, in a pediatric subject, the method comprising administering to the pediatric subject a nutritional composition comprising polar lipids, prebiotics, especially polydextrose (PDX) and galacto-oligosaccharides (GOS), lactoferrin from a non-human source, and long-chain polyunsaturated fatty acids (LCPUFAs). In certain embodiments, the method comprises administering a nutritional composition comprising:

a. up to about 7 g/100 kcal of a fat or lipid source, more preferably about 3 g/100 kcal to about 7 g/100 kcal of a fat or lipid source, wherein the fat or lipid source comprises at least about 0.5 mg/100 kcal, and more preferably from about 0.5 mg/100 kcal to about 470 mg/100 kcal, of polar lipids;

b. up to about 5 g/100 kcal of a protein source, more preferably about 1 g/100 kcal to about 5 g/100 kcal of a protein source;

c. at least about 10 mg/100 kcal of lactoferrin, more preferably from about 10 mg/100 kcal to about 200 mg/100 kcal of lactoferrin;

d. about 0.1 g/100 kcal to about 1 g/100 kcal of a prebiotic composition comprising PDX and GOS; and e. at least about 5 mg/100 kcal of an LCPUFA comprising docosahexaenoic acid (DHA), more preferably from about 5 mg/100 kcal to about 75 mg/100 kcal of LCPUFAs comprising DHA.

In other embodiments, the disclosure is directed to methods for supporting healthy growth and development in a pediatric subject by administering to the subject a nutritional composition comprising polar lipids with prebiotics, lactoferrin from a non-human source, and LCPUFAs.

It is to be understood that both the foregoing general description and the following detailed description present embodiments of the disclosure and are intended to provide an overview or framework for understanding the nature and character of the disclosure as it is claimed. The description serves to explain the principles and operations of the claimed subject matter. Other and further features and advantages of the present disclosure will be readily apparent to those skilled in the art upon a reading of the following disclosure.

BRIEF DESCRIPTION OF THE DRAWINGS

FIG. 1 provides a graph illustrating indicator species analysis of the lactobacilli community of 21d old piglets fed either a bovine milk-based formula (C) or bovine milk-based formula supplemented with GOS and PDX (G+P). (a) Indicator species scores for the genera *Lactobacillus* from ileum contents. Color change demonstrates the more a species is indicative of a diet. The higher the indicator score (i.e. darker color), the more that species is indicative of that group. (b) Indicator species scores for the genera *Lactobacillus* from ascending colon contents. Color change demonstrates the more a species is indicative of a diet. The higher the indicator score (i.e. darker color), the more that species is indicative of that group.

DETAILED DESCRIPTION

Figure 2:
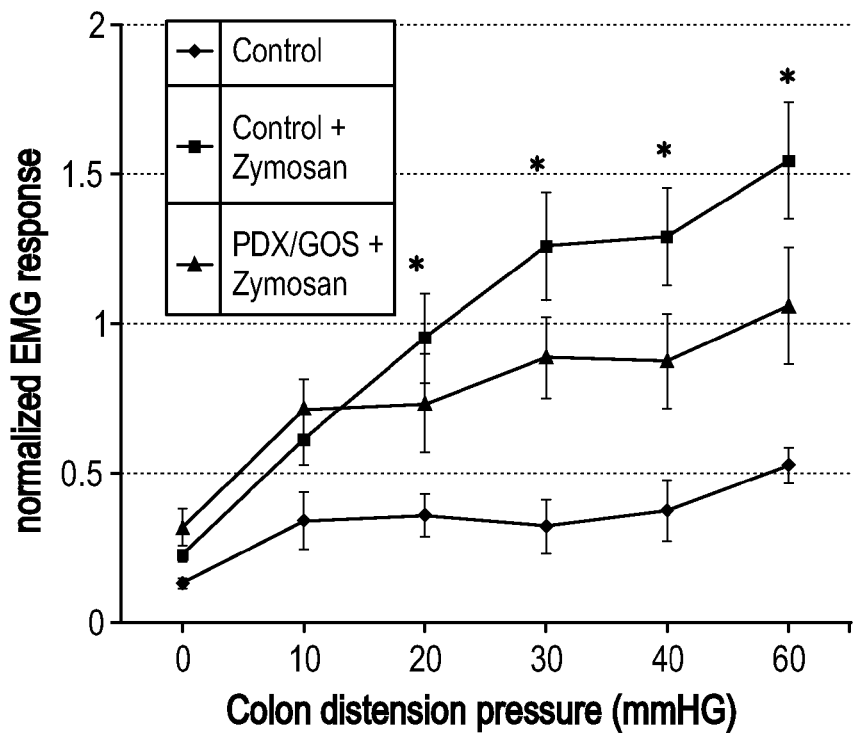
FIG. 2 is a graph that shows an effect of GOS/PDX diet on the viscera-motor response in neonatal rats with colitis.

Reference now will be made in detail to the embodiments of the present disclosure, one or more examples of which are set forth hereinbelow. Each example is provided by way of explanation of the nutritional composition of the present disclosure and is not a limitation. In fact, it will be apparent to those skilled in the art that various modifications and variations can be made to the teachings of the present disclosure without departing from the scope of the disclosure. For instance, features illustrated or described as part of one embodiment, can be used with another embodiment to yield a still further embodiment.

Thus, it is intended that the present disclosure covers such modifications and variations as come within the scope of the appended claims and their equivalents. Other objects, features and aspects of the present disclosure are disclosed in or are obvious from the following detailed description. It is to be understood by one of ordinary skill in the art that the present discussion is a description of exemplary embodiments only and is not intended as limiting the broader aspects of the present disclosure.

The present disclosure relates generally to nutritional compositions, especially milk-based nutritional compositions that are suitable for administration to a pediatric subject. Additionally, the disclosure relates to methods of supporting and promoting gastrointestinal health, cognitive development and brain function and to methods of reducing psychological stress in a pediatric subject via administration of milk-based nutritional compositions.

"Nutritional composition" means a substance or formulation that satisfies at least a portion of a subject's nutrient requirements. The terms "nutritional(s)", "nutritional formula(s)", "enteral nutritional(s)", and "nutritional supplement(s)" are used as non-limiting examples of nutritional composition(s) throughout the present disclosure. Moreover, "nutritional composition(s)" may refer to liquids, powders, gels, pastes, solids, concentrates, suspensions, or ready-to-use forms of enteral formulas, oral formulas, formulas for infants, formulas for pediatric subjects, formulas for children, growing-up milks and/or formulas for adults.

The term "enteral" means deliverable through or within the gastrointestinal, or digestive, tract. "Enteral administration" includes oral feeding, intragastric feeding, transpyloric administration, or any other administration into the digestive tract. "Administration" is broader than "enteral administration" and includes parenteral administration or any other route of administration by which a substance is taken into a subject's body.

"Pediatric subject" means a human no greater than 13 years of age. In some embodiments, a pediatric subject refers to a human subject that is between birth and 8 years old. In other embodiments, a pediatric subject refers to a human subject between 1 and 6 years of age. In still further embodiments, a pediatric subject refers to a human subject between 6 and 12 years of age. The term "pediatric subject" may refer to infants (preterm or full term) and/or children, as described below.

"Infant" means a human subject ranging in age from birth to not more than one year and includes infants from 0 to 12 months corrected age. The phrase "corrected age" means an infant's chronological age minus the amount of time that the infant was born premature. Therefore, the corrected age is the age of the infant if it had been carried to full term. The term infant includes low birth weight infants, very low birth weight infants, extremely low birth weight infants and preterm infants. "Preterm" means an infant born before the end of the 37th week of gestation. "Late preterm" means an infant form between the 34th week and the 36th week of gestation. "Full term" means an infant born after the end of the 37th week of gestation. "Low birth weight infant" means an infant born weighing less than 2500 grams (approximately 5 lbs, 8 ounces). "Very low birth weight infant" means an infant born weighing less than 1500 grams (approximately 3 lbs, 4 ounces). "Extremely low birth weight infant" means an infant born weighing less than 1000 grams (approximately 2 lbs, 3 ounces).

"Child" means a subject ranging in age from 12 months to 13 years. In some embodiments, a child is a subject between the ages of 1 and 12 years old. In other embodiments, the terms "children" or "child" refer to subjects that are between one and about six years old, or between about seven and about 12 years old. In other embodiments, the terms "children" or "child" refer to any range of ages between 12 months and about 13 years.

"Children's nutritional product" refers to a composition that satisfies at least a portion of the nutrient requirements of a child. A growing-up milk is an example of a children's nutritional product.

The term "degree of hydrolysis" refers to the extent to which peptide bonds are broken by a hydrolysis method.

The term "partially hydrolyzed" means having a degree of hydrolysis which is greater than 0% but less than about 50%.

The term "extensively hydrolyzed" means having a degree of hydrolysis which is greater than or equal to about 50%.

The term "protein-free" means containing no measurable amount of protein, as measured by standard protein detection methods such as sodium dodecyl (lauryl) sulfate-polyacrylamide gel electrophoresis (SDS-PAGE) or size exclusion chromatography. In some embodiments, the nutritional composition is substantially free of protein, wherein "substantially free" is defined hereinbelow.

"Infant formula" means a composition that satisfies at least a portion of the nutrient requirements of an infant. In the United States, the content of an infant formula is dictated by the federal regulations set forth at 21 C.F.R. Sections 100, 106, and 107. These regulations define macronutrient, vitamin, mineral, and other ingredient levels in an effort to simulate the nutritional and other properties of human breast milk.

The term "growing-up milk" refers to a broad category of nutritional compositions intended to be used as a part of a diverse diet in order to support the normal growth and development of a child between the ages of about 1 and about 6 years of age.

"Milk-based" means comprising at least one component that has been drawn or extracted from the mammary gland of a mammal. In some embodiments, a milk-based nutritional composition comprises components of milk that are derived from domesticated ungulates, ruminants or other mammals or any combination thereof. Moreover, in some embodiments, milk-based means comprising bovine casein, whey, lactose, or any combination thereof. Further, "milk-based nutritional composition" may refer to any composition comprising any milk-derived or milk-based product known in the art.

"Nutritionally complete" means a composition that may be used as the sole source of nutrition, which would supply essentially all of the required daily amounts of vitamins, minerals, and/or trace elements in combination with proteins, carbohydrates, and lipids. Indeed, "nutritionally complete" describes a nutritional composition that provides adequate amounts of carbohydrates, lipids, essential fatty acids, proteins, essential amino acids, conditionally essential amino acids, vitamins, minerals and energy required to support normal growth and development of a subject.

Therefore, a nutritional composition that is "nutritionally complete" for a preterm infant will, by definition, provide qualitatively and quantitatively adequate amounts of carbohydrates, lipids, essential fatty acids, proteins, essential amino acids, conditionally essential amino acids, vitamins, minerals, and energy required for growth of the preterm infant.

A nutritional composition that is "nutritionally complete" for a full term infant will, by definition, provide qualitatively and quantitatively adequate amounts of all carbohydrates, lipids, essential fatty acids, proteins, essential amino acids, conditionally essential amino acids, vitamins, minerals, and energy required for growth of the full term infant.

A nutritional composition that is "nutritionally complete" for a child will, by definition, provide qualitatively and quantitatively adequate amounts of all carbohydrates, lipids, essential fatty acids, proteins, essential amino acids, conditionally essential amino acids, vitamins, minerals, and energy required for growth of a child.

As applied to nutrients, the term "essential" refers to any nutrient that cannot be synthesized by the body in amounts sufficient for normal growth and to maintain health and that, therefore, must be supplied by the diet. The term "conditionally essential" as applied to nutrients means that the nutrient must be supplied by the diet under conditions when adequate amounts of the precursor compound is unavailable to the body for endogenous synthesis to occur.

"Probiotic" means a microorganism with low or no pathogenicity that exerts a beneficial effect on the health of the host.

The term "inactivated probiotic" means a probiotic wherein the metabolic activity or reproductive ability of the referenced probiotic has been reduced or destroyed. The "inactivated probiotic" does, however, still retain, at the cellular level, its cell structure or other structure associated with the cell, for example exopolysaccharide and at least a portion its biological glycol-protein and DNA/RNA structure. As used herein, the term "inactivated" is synonymous with "non-viable".

"Prebiotic" means a non-digestible food ingredient that beneficially affects the host by selectively stimulating the growth and/or activity of one or a limited number of bacteria in the digestive tract that can improve the health of the host.

"Polar lipids" are the main constituents of natural membranes, occurring in all living organisms. The polar lipids in milk (i.e., milk polar lipids) are mainly situated in the milk fat globule membrane (MFGM). This is a highly complex biological membrane that surrounds the fat globule, hereby stabilizing it in the continuous phase of the milk. Polar lipids are also present in other sources than milk such as eggs, meat and plants.

Polar lipids are generally divided into phospholipids and sphingolipids (including gangliosides), which are amphiphilic molecules with a hydrophobic tail and a hydrophilic head group. The glycerophospholipids consist of a glycerol backbone on which two fatty acids are esterified on positions sn-1 and sn-2. These fatty acids are more unsaturated than the triglyceride fraction of milk. On the third hydroxyl, a phosphate residue with different organic groups (choline, serine, ethanolamine, etc.) may be linked. Generally, the fatty acid chain on the sn-1 position is more saturated compared with that at the sn-2 position. Lysophospholipids contain only one acyl group, predominantly situated at the sn-1 position. The head group remains similar. The characteristic structural unit of sphingolipids is the sphingoid base, a long-chain (12-22 carbon atoms) aliphatic amine containing two or three hydroxyl groups. Sphingosine (d18:1), is the most prevalent sphingoid base in mammalian sphingolipids, containing 18 carbon atoms, two hydroxyl groups and one double bond. A ceramide is formed when the amino group of this sphingoid base is linked with, usually, a saturated fatty acid. On this ceramide unit, an organophosphate group can be bound to form a sphingophospholipid (e.g., phosphocholine in the case of sphingomyelin) or a saccharide to form the sphingoglycolipids (glycosylceramides). Monoglycosylceramides, like glucosylceramide or galactosylceramide are often denoted as cerebrosides while tri- and tetraglycosylceramides with a terminal galactosamine residue are denoted as globosides. Finally, gangliosides are highly complex oligoglycosylceramides, containing one or more sialic acid groups in addition to glucose, galactose and galactosamine.

"Phytonutrient" means a chemical compound that occurs naturally in plants. Phytonutrients may be included in any plant-derived substance or extract. The term "phytonutrient(s)" encompasses several broad categories of compounds produced by plants, such as, for example, polyphenolic compounds, anthocyanins, proanthocyanidins, and flavan-3-ols (i.e. catechins, epicatechins), and may be derived from, for example, fruit, seed or tea extracts. Further, the term phytonutrient includes all carotenoids, phytosterols, thiols, and other plant-derived compounds. Moreover, as a skilled artisan will understand, plant extracts may include phytonutrients, such as polyphenols, in addition to protein, fiber or other plant-derived components. Thus, for example, apple or grape seed extract(s) may include beneficial phytonutrient components, such as polyphenols, in addition to other plant-derived substances.

"β-glucan" means all β-glucan, including specific types of β-glucan, such as β-1,3-glucan or β-1,3;1,6-glucan. Moreover, β-1,3;1,6-glucan is a type of β-1,3-glucan. Therefore, the term "β-1,3-glucan" includes β-1,3;1,6-glucan.

"Pectin" means any naturally-occurring oligosaccharide or polysaccharide that comprises galacturonic acid that may be found in the cell wall of a plant. Different varieties and grades of pectin having varied physical and chemical properties are known in the art. Indeed, the structure of pectin can vary significantly between plants, between tissues, and even within a single cell wall. Generally, pectin is made up of negatively charged acidic sugars (galacturonic acid), and some of the acidic groups are in the form of a methyl ester group. The degree of esterification of pectin is a measure of the percentage of the carboxyl groups attached to the galactopyranosyluronic acid units that are esterified with methanol.

Pectin having a degree of esterification of less than 50% (i.e., less than 50% of the carboxyl groups are methylated to form methyl ester groups) are classified as low-ester, low methoxyl, or low methylated ("LM") pectins, while those having a degree of esterification of 50% or greater (i.e., more than 50% of the carboxyl groups are methylated) are classified as high-ester, high methoxyl or high methylated ("HM") pectins. Very low ("VL") pectins, a subset of low methylated pectins, have a degree of esterification that is less than approximately 15%.

As used herein, "lactoferrin from a non-human source" means lactoferrin which is produced by or obtained from a source other than human breast milk. For example, lactoferrin for use in the present disclosure includes human lactoferrin produced by a genetically modified organism as well as non-human lactoferrin. The term "organism", as used herein, refers to any contiguous living system, such as animal, plant, fungus or micro-organism. The term "non-human lactoferrin", as used herein, refers to lactoferrin having an amino acid sequence that is different than the amino acid sequence of human lactoferrin.

As used herein, "non-human lactoferrin" means lactoferrin that has an amino acid sequence that is different than the amino acid sequence of human lactoferrin.

"Pathogen" means an organism that causes a disease state or pathological syndrome. Examples of pathogens may include bacteria, viruses, parasites, fungi, microbes or combination(s) thereof.

"Modulate" or "modulating" means exerting a modifying, controlling and/or regulating influence. In some embodiments, the term "modulating" means exhibiting an increasing or stimulatory effect on the level/amount of a particular component. In other embodiments, "modulating" means exhibiting a decreasing or inhibitory effect on the level/amount of a particular component.

All percentages, parts and ratios as used herein are by weight of the total formulation, unless otherwise specified.

All amounts specified as administered "per day" may be delivered in one unit dose, in a single serving or in two or more doses or servings administered over the course of a 24 hour period.

The nutritional composition of the present disclosure may be substantially free of any optional or selected ingredients described herein, provided that the remaining nutritional composition still contains all of the required ingredients or features described herein. In this context, and unless otherwise specified, the term "substantially free" means that the selected composition may contain less than a functional amount of the optional ingredient, typically less than 0.1% by weight, and also, including zero percent by weight of such optional or selected ingredient.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The methods and compositions of the present disclosure, including components thereof, can comprise, consist of, or consist essentially of the essential elements and limitations of the embodiments described herein, as well as any additional or optional ingredients, components or limitations described herein or otherwise useful in nutritional compositions.

As used herein, the term "about" should be construed to refer to both of the numbers specified as the endpoint(s) of any range. Any reference to a range should be considered as providing support for any subset within that range.

The present disclosure is directed to milk-based nutritional compositions comprising polar lipids, a prebiotic, lactoferrin from a non-human source and a source of LCPUFAs, to uses thereof, and to methods comprising administration of those nutritional compositions. The nutritional compositions of the present disclosure support overall health and development in a pediatric human subject, such as an infant (preterm and/or term) or a child.

The intestinal microflora plays a crucial role in the postnatal development of most gastrointestinal functions. Accordingly, the nutritional composition of the present disclosure supports gastrointestinal health and development. Moreover, a healthy intestinal flora supports an adequate gut-brain communication, affecting brain function and, consequently, psychological stress responses, resulting in modified behavior. Administration of the compositions of the present disclosure together can modulate the intestinal flora of a pediatric subject by increasing beneficial bacteria and/or reducing adhesion of pathogens in the gastrointestinal system. Thus, in some embodiments, the present disclosure is directed to a method for modulating psychological stress responses. And in certain embodiments, the disclosed combination has additive and/or synergistic beneficial effects that support gastrointestinal development. In certain embodiments, the disclosure is related to a method for supporting cognitive development and brain function, and gastrointestinal health and/or development in a pediatric subject. The method comprises administering polar lipids with prebiotics, especially PDX and GOS, lactoferrin from a non-human source, and LCPUFAs to a pediatric subject.

Moreover, during early life, infants and children experience many stressful situations due to, for example, a changing environment or being hungry or tired. Consequently, stress hormones are released, which may negatively affect brain development and/or cause other long-term detrimental effects in a pediatric subject. Yet the nutritional composition of the present disclosure can reduce or suppress psychological stress and/or modulate plasma corticosterone levels, thereby further promoting healthy brain and cognitive growth and development in a pediatric subject.

Thus, in some embodiments, the present disclosure includes a method for reducing psychological stress in a pediatric subject comprising administering to the subject an effective amount of the disclosed nutritional composition. In other embodiments, the disclosure is directed to a method for improving brain and/or cognitive function in a pediatric subject by administering an effective amount of the composition to the subject.

In infants, immaturity of the gut often causes gastrointestinal symptoms that affect their nutritional status with consequences for their overall health. The present disclosure is directed to a nutritional composition that supports, in some embodiments, gut development and communication of the gut with the brain via the gut-brain axis. Moreover, the nutritional compositions of the present disclosure may positively impact brain-related functions. Thus, in some embodiments, the present disclosure is directed to a method of modulating gut-brain communication.

Consumption of the milk-based nutritional composition of the present disclosure may increase specific species of polar lipids, lactoferrin, DHA, and B-vitamins in brain regions involved in cognition, memory, learning, emotional regulation and motor coordination. In addition, the use of prebiotics, especially PDX and GOS alter the production of biogenic amines and neurotransmitters within the central nervous system, and such changes may explain the beneficial effects of feeding PDX/GOS on social skills, anxiety and memory functions. Moreover, the inclusion of lactoferrin can improve a subject's adaptability to a stressful situation and separately improve learning capacity. Yet further, polar lipids improve motor coordination and link to the other nutrients to provide a yet further expansion of benefits for this unique combination. In summary, the disclosed nutritional composition may play an important role during infancy and childhood by modifying intestinal microflora, optimizing brain composition, and improving a variety of brain-related behaviors and functions.

Polar lipids should be present in the nutritional composition at a level of about 0.5 mg/100 kcal to about 470 mg/100 kcal; in some embodiments, polar lipids are present at a level of about 10 mg/100 kcal to about 350 mg/100 kcal; In yet other embodiments, polar lipids are present in the nutritional composition at a level of about 20 mg/100 kcal to about 260 mg/100 kcal. In certain embodiments, the polar lipids comprise milk polar lipids.

In some embodiments, the polar lipids comprise gangliosides and phospholipids, where the gangliosides are present at a level of about 0.5 mg/100 kcal to about 18 mg/100 kcal, and the phospholipids are present at a level of about 10 mg/100 kcal to about 450 mg/100 kcal. In another embodiment, the gangliosides are present at 1 mg/100 kcal to about 9 mg/100 kcal, and the phospholipids are present at about 20 mg/100 kcal to about 250 mg/100 kcal.

In yet further embodiments, the levels of gangliosides and phospholipids can be keyed to the more specific age of the subject infant or child. For instance, for an infant, the gangliosides can be present at a level of about 0.5 mg/100 kcal to about 12 mg/100 kcal, more preferably from about 1 mg/100 kcal to about 9 mg/100 kcal, and the phospholipids can be present at a level of about 20 mg/100 kcal to about 250 mg/100 kcal, more preferably about 20 mg/100 kcal to about 50 mg/100 kcal. For a child, the gangliosides can be present at a level of about 1 mg/100 kcal to about 18 mg/100 kcal, more preferably from about 1.5 mg/100 kcal to about 12 mg/100 kcal, and the phospholipids can be present at a level of about 20 mg/100 kcal to about 450 mg/100 kcal, more preferably about 20 mg/100 kcal to about 250 mg/100 kcal.

Indeed, for an infant between birth and 6 months of age, the gangliosides can be present at a level of about 0.5 mg/100 kcal to about 9 mg/100 kcal, more preferably from about 1 mg/100 kcal to about 5 mg/100 kcal, and the phospholipids can be present at a level of about 20 mg/100 kcal to about 150 mg/100 kcal, more preferably about 25 mg/100 kcal to about 75 mg/100 kcal; for an infant between 6 and 12 months of age, the gangliosides can be present at a level of about 0.9 mg/100 kcal to about 12 mg/100 kcal, more preferably from about 1.3 mg/100 kcal to about 5.5 mg/100 kcal, and the phospholipids can be present at a level of about 25 mg/100 kcal to about 110 mg/100 kcal. Likewise, with children from 12 to 24 months of age, the gangliosides can be present at a level of about 1 mg/100 kcal to about 13 mg/100 kcal, more preferably from about 1.5 mg/100 kcal to about 6.5 mg/100 kcal, and the phospholipids can be present at a level of about 35 mg/100 kcal to about 135 mg/100 kcal, whereas for children 24 months to 36 months, the gangliosides can be present at a level of about 1.7 mg/100 kcal to about 18 mg/100 kcal, more preferably from about 2 mg/100 kcal to about 9 mg/100 kcal, and the phospholipids can be present at a level of about 35 mg/100 kcal to about 250 mg/100 kcal.

As noted, lactoferrin is also included in the nutritional composition of the present disclosure. Lactoferrins are single chain polypeptides of about 80 kD containing 1-4 glycans, depending on the species. The 3-D structures of lactoferrin of different species are very similar, but not identical. Each lactoferrin comprises two homologous lobes, called the N- and C-lobes, referring to the N-terminal and C-terminal part of the molecule, respectively. Each lobe further consists of two sub-lobes or domains, which form a cleft where the ferric ion ($Fe^{3+}$) is tightly bound in synergistic cooperation with a (bi)carbonate anion. These domains are called N1, N2, C1 and C2, respectively. The N-terminus of lactoferrin has strong cationic peptide regions that are responsible for a number of important binding characteristics. Lactoferrin has a very high isoelectric point (~pI 9) and its cationic nature plays a major role in its ability to defend against bacterial, viral, and fungal pathogens. There are several clusters of cationic amino acids residues within the N-terminal region of lactoferrin mediating the biological activities of lactoferrin against a wide range of microorganisms. For instance, the N-terminal residues 1-47 of human lactoferrin (1-48 of bovine lactoferrin) are critical to the iron-independent biological activities of lactoferrin. In human lactoferrin, residues 2 to 5 (RRRR) and 28 to 31 (RKVR) are arginine-rich cationic domains in the N-terminus especially critical to the antimicrobial activities of lactoferrin. A similar region in the N-terminus is found in bovine lactoferrin (residues 17 to 42; FKCRRWQWRMK-KLGAPSITCVRRAFA).

As described in "*Perspectives on Interactions Between Lactoferrin and Bacteria*" which appeared in the publication BIOCHEMISTRY AND CELL BIOLOGY, pp 275-281 (2006), lactoferrins from different host species may vary in their amino acid sequences though commonly possess a relatively high isoelectric point with positively charged amino acids at the end terminal region of the internal lobe. Suitable non-human lactoferrins for use in the present disclosure include, but are not limited to, those having at least 48% homology with the amino acid sequence of human lactoferrin. For instance, bovine lactoferrin ("bLF") has an amino acid composition which has about 70% sequence homology to that of human lactoferrin. In some embodiments, the non-human lactoferrin has at least 55% homology with human lactoferrin and in some embodiments, at least 65% homology. Non-human lactoferrins acceptable for use in the present disclosure include, without limitation, bLF, porcine lactoferrin, equine lactoferrin, buffalo lactoferrin, goat lactoferrin, murine lactoferrin and camel lactoferrin.

In one embodiment, lactoferrin is present in the nutritional composition in an amount of at least about 15 mg/100 kCal. In certain embodiments, the nutritional composition may include between about 15 and about 300 mg lactoferrin per 100 kCal. In another embodiment, where the nutritional composition is an infant formula, the nutritional composition may comprise lactoferrin in an amount of from about 60 mg to about 150 mg lactoferrin per 100 kCal; in yet another embodiment, the nutritional composition may comprise about 60 mg to about 100 mg lactoferrin per 100 kCal.

In some embodiments, the nutritional composition can include lactoferrin in the quantities of from about 0.5 mg to about 1.5 mg per milliliter of formula. In nutritional compositions replacing human milk, lactoferrin may be present in quantities of from about 0.6 mg to about 1.3 mg per milliliter of formula. In certain embodiments, the nutritional composition may comprise between about 0.1 and about 2 grams lactoferrin per liter. In some embodiments, the nutritional composition includes between about 0.6 and about 1.5 grams lactoferrin per liter of formula.

The bLF that is used in certain embodiments may be any bLF isolated from whole milk and/or having a low somatic cell count, wherein "low somatic cell count" refers to a somatic cell count less than 200,000 cells/mL. By way of example, suitable bLF is available from Tatua Co-operative Dairy Co. Ltd., in Morrinsville, New Zealand, from FrieslandCampina Domo in Amersfoort, Netherlands or from Fonterra Co-Operative Group Limited in Auckland, New Zealand.

Lactoferrin for use in the present disclosure may be, for example, isolated from the milk of a non-human animal or produced by a genetically modified organism. For example, in U.S. Pat. No. 4,791,193, incorporated by reference herein in its entirety, Okonogi et al. discloses a process for producing bovine lactoferrin in high purity. Generally, the process as disclosed includes three steps. Raw milk material is first contacted with a weakly acidic cationic exchanger to absorb lactoferrin followed by the second step where washing takes place to remove nonabsorbed substances. A desorbing step follows where lactoferrin is removed to produce purified bovine lactoferrin. Other methods may include steps as described in U.S. Pat. Nos. 7,368,141, 5,849,885, 5,919,913 and 5,861,491, the disclosures of which are all incorporated by reference in their entirety.

In certain embodiments, lactoferrin utilized in the present disclosure may be provided by an expanded bed absorption ("EBA") process for isolating proteins from milk sources. EBA, also sometimes called stabilized fluid bed adsorption, is a process for isolating a milk protein, such as lactoferrin, from a milk source comprises establishing an expanded bed adsorption column comprising a particulate matrix, applying a milk source to the matrix, and eluting the lactoferrin from the matrix with an elution buffer comprising about 0.3 to about 2.0 M sodium chloride. Any mammalian milk source may be used in the present processes, although in particular embodiments, the milk source is a bovine milk source. The milk source comprises, in some embodiments, whole milk, reduced fat milk, skim milk, whey, casein, or mixtures thereof.

In particular embodiments, the target protein is lactoferrin, though other milk proteins, such as lactoperoxidases or lactalbumins, also may be isolated. In some embodiments, the process comprises the steps of establishing an expanded bed adsorption column comprising a particulate matrix, applying a milk source to the matrix, and eluting the lactoferrin from the matrix with about 0.3 to about 2.0M sodium chloride. In other embodiments, the lactoferrin is eluted with about 0.5 to about 1.0 M sodium chloride, while in further embodiments, the lactoferrin is eluted with about 0.7 to about 0.9 M sodium chloride.

The expanded bed adsorption column can be any known in the art, such as those described in U.S. Pat. Nos. 7,812,138, 6,620,326, and 6,977,046, the disclosures of which are hereby incorporated by reference herein. In some embodiments, a milk source is applied to the column in an expanded mode, and the elution is performed in either expanded or packed mode. In particular embodiments, the elution is performed in an expanded mode. For example, the expansion ratio in the expanded mode may be about 1 to about 3, or about 1.3 to about 1.7. EBA technology is further described in international published application nos. WO 92/00799, WO 02/18237, WO 97/17132, which are hereby incorporated by reference in their entireties.

The isoelectric point of lactoferrin is approximately 8.9. Prior EBA methods of isolating lactoferrin use 200 mM sodium hydroxide as an elution buffer. Thus, the pH of the system rises to over 12, and the structure and bioactivity of lactoferrin may be comprised, by irreversible structural changes. It has now been discovered that a sodium chloride solution can be used as an elution buffer in the isolation of lactoferrin from the EBA matrix. In certain embodiments, the sodium chloride has a concentration of about 0.3 M to about 2.0 M. In other embodiments, the lactoferrin elution buffer has a sodium chloride concentration of about 0.3 M to about 1.5 M, or about 0.5 m to about 1.0 M.

The nutritional composition may also contain one or more prebiotics (also referred to as a prebiotic component) in certain embodiments. Prebiotics exert health benefits, which may include, but are not limited to, selective stimulation of the growth and/or activity of one or a limited number of beneficial gut bacteria, stimulation of the growth and/or activity of ingested probiotic microorganisms, selective reduction in gut pathogens, and favorable influence on gut short chain fatty acid profile. Such prebiotics may be naturally-occurring, synthetic, or developed through the genetic manipulation of organisms and/or plants, whether such new source is now known or developed later. Prebiotics useful in the present disclosure may include oligosaccharides, polysaccharides, and other prebiotics that contain fructose, xylose, soya, galactose, glucose and mannose.

More specifically, prebiotics useful in the present disclosure may include polydextrose, polydextrose powder, lactulose, lactosucrose, raffinose, gluco-oligosaccharide, inulin, fructo-oligosaccharide, isomalto-oligosaccharide, soybean oligosaccharides, lactosucrose, xylo-oligosaccharide, chito-oligosaccharide, manno-oligosaccharide, aribino-oligosaccharide, siallyl-oligosaccharide, fuco-oligosaccharide, galacto-oligosaccharide and gentio-oligosaccharides.

In an embodiment, the total amount of prebiotics present in the nutritional composition may be from about 1.0 g/L to about 10.0 g/L of the composition. More preferably, the total amount of prebiotics present in the nutritional composition may be from about 2.0 g/L and about 8.0 g/L of the composition. In some embodiments, the total amount of prebiotics present in the nutritional composition may be from about 0.01 g/100 kcal to about 0.15 g/100 kcal. In certain embodiments, the total amount of prebiotics present in the nutritional composition may be from about 0.03 g/100 kcal to about 0.07 g/100 kcal. Moreover, the nutritional composition may comprise a prebiotic component comprising PDX. In some embodiments, the prebiotic component comprises at least 20% w/w PDX, GOS or a mixture thereof.

If PDX is used in the prebiotic composition, the amount of PDX in the nutritional composition may, in an embodiment, be within the range of from about 0.015 g/100 kcal to about 0.15 g/100 kcal. In another embodiment, the amount of polydextrose is within the range of from about 0.02 g/100 kcal to about 0.06 g/100 kcal. In some embodiments, PDX may be included in the nutritional composition in an amount sufficient to provide between about 1.0 g/L and 10.0 g/L. In another embodiment, the nutritional composition contains an amount of PDX that is between about 2.0 g/L and 8.0 g/L. And in still other embodiments, the amount of PDX in the nutritional composition may be from about 0.015 g/100 kcal to about 0.05 g/100 kcal.

In other embodiments, the prebiotic component may comprise GOS. If GOS is used in the prebiotic composition, the amount of GOS in the nutritional composition may, in an embodiment, be from about 0.015 g/100 kcal to about 0.15 g/100 kcal. In another embodiment, the amount of GOS in the nutritional composition may be from about 0.02 g/100 kcal to about 0.05 g/100 kcal. In other embodiments, the amount of GOS in the nutritional composition may be from about 0.015 g/100 kcal to about 0.1 g/100 kcal or from about 0.01 mg/100 kcal to about 0.05 mg/100 kcal.

In a particular embodiment of the present invention, PDX is administered in combination with GOS.

In a particular embodiment, GOS and PDX are supplemented into the nutritional composition in a total amount of at least about 0.02 g/100 kcal or about 0.02 g/100 kcal to about 0.15 mg/100 kcal. In some embodiments, the nutritional composition may comprise GOS and PDX in a total amount of from about 0.06 to about 0.08 mg/100 kcal.

The nutritional composition of the disclosure also contains a source of LCPUFAs; especially a source of LCPUFAs that comprises docosahexaenoic acid. Other suitable LCPUFAs include, but are not limited to, α-linoleic acid, γ-linoleic acid, linoleic acid, linolenic acid, eicosapentaenoic acid (EPA) and arachidonic acid (ARA).

In an embodiment, especially if the nutritional composition is an infant formula, the nutritional composition is supplemented with both DHA and ARA. In this embodiment, the weight ratio of ARA:DHA may be between about 1:3 and about 9:1. In a particular embodiment, the ratio of ARA:DHA is from about 1:2 to about 4:1.

The amount of long chain polyunsaturated fatty acid in the nutritional composition is advantageously at least about 5 mg/100 kcal, and may vary from about 5 mg/100 kcal to about 100 mg/100 kcal, more preferably from about 10 mg/100 kcal to about 50 mg/100 kcal.

The nutritional composition may be supplemented with oils containing DHA and/or ARA using standard techniques known in the art. For example, DHA and ARA may be added to the composition by replacing an equivalent amount of an oil, such as high oleic sunflower oil, normally present in the composition. As another example, the oils containing DHA and ARA may be added to the composition by replacing an equivalent amount of the rest of the overall fat blend normally present in the composition without DHA and ARA.

If utilized, the source of DHA and/or ARA may be any source known in the art such as marine oil, fish oil, single cell oil, egg yolk lipid, and brain lipid. In some embodiments, the DHA and ARA are sourced from single cell Martek oils, DHASCO® and ARASCO®, or variations thereof. The DHA and ARA can be in natural form, provided that the remainder of the LCPUFA source does not result in any substantial deleterious effect on the infant. Alternatively, the DHA and ARA can be used in refined form.

In an embodiment, sources of DHA and ARA are single cell oils as taught in U.S. Pat. Nos. 5,374,567; 5,550,156; and 5,397,591, the disclosures of which are incorporated herein in their entirety by reference. However, the present disclosure is not limited to only such oils.

Furthermore, some embodiments of the nutritional composition may mimic certain characteristics of human breast milk. However, to fulfill the specific nutrient requirements of some subjects, the nutritional composition may comprise a higher amount of some nutritional components than does human milk. For example, the nutritional composition may comprise a greater amount of DHA than does human breast milk. Accordingly, the enhanced level of DHA of the nutritional composition may compensate for an existing nutritional DHA deficit.

The selection of nutrients described hereinabove is believed to provide a comprehensive set of novel benefits for infants and children not possible with current offerings. First, consumption of this milk based nutritional composition may increase specific species of polar lipids, lactoferrin, DHA, and B-vitamins in brain regions involved in cognition, memory, learning, emotional regulation and motor coordination. Such physical changes in those brain regions may directly explain the benefits that have been discovered. Second, the combination of PDX and GOS may alter the production of biogenic amines and neurotransmitters within the central nervous system ("CNS"), and such changes may explain the beneficial effects of feeding PDX/GOS on social skills, anxiety and memory functions. Third, novel effects of lactoferrin can improve the adaptability to a stressful situation and separately improve learning capacity, which are unique attributes from the other components. Lastly, further distinct benefits of milk polar lipids to improve motor coordination have been observed. In summary, the current nutritional composition may play an important role during infancy and childhood by modifying intestinal microflora, optimizing brain composition, and improving a variety of brain-related behaviors and functions.

The unique combination of nutrients in the disclosed nutritional composition is believed to be capable of providing novel and unexpected brain-related benefits for infants and children. Moreover, the benefit of this nutritional composition is believed to be obtained during infancy, and also by including it as part of a diverse diet as the child and its brain continues to grow and develop.

Administering a nutritional composition comprising polar lipids with prebiotics, PDX and GOS, lactoferrin from a non-human source, and LCPUFAs to a pediatric subject has multiple purposes, the combination of which are not currently described or available: brings the overall formulation closer to human milk in composition and functionality; addresses specific infant and children nutritional gaps; improves the infant and children's microbiota community with or without the need for a probiotic; improves specific brain functions such as (but not limited to) memory function, learning capacity, social interaction skills, reduced anxiety, visual acuity, motor skills, hand-eye coordination, general fussiness (reduced visceral pain sensitivity), sleep quality; enhances multi-nutrient bioavailability, such as B vitamins, and associated benefits for optimal brain development and functions; and modulates/optimizes brain composition leading to enhanced communications within the CNS and between the CNS and gut, through modulation of CNS neurotransmitters.

The combination of nutrients in the nutritional composition combine in synergistic ways to provide the foregoing benefits. For instance, providing lactoferrin with a prebiotic comprising PDX and GOS can synergistically reduce anxiety in infants and have an anti-bacterial effect for pathogens while simultaneously enhancing the colonization in the gut of beneficial organisms such as the *Bifidobacterium* spp., as compared to either component by itself. The combination of lactoferrin with polar lipids can have enhanced anti-pathogen effects. The combination of a prebiotic comprising PDX and GOS can combine with polar lipids to more effectively modulate gut microbiota to provide a more beneficial gut environment, to an extent not anticipated by use of either nutrient separately; indeed, the combination of PDX and GOS with polar lipids may synergistically enhance colonization of bifidobacteria beyond either component by itself.

Lactoferrin, polar lipids and prebiotics act in an orchestrated manner; all induce bifidogenic bacteria which in turn utilize the prebiotics and part of the polar lipids for energy resulting in production of reactive oxygen species that would be captured by the antioxidative function of lactoferrin. Thus, the components of nutritional composition of the present disclosure may act in an orchestrated manner to enhance bifidobacterial population.

In addition, the mechanism at work in the anti-pathogen effect of the lactoferrin/prebiotic combination is different from the anti-pathogen mechanism at work in the lactoferrin/polar lipid combination. More specifically, the lactoferrin/prebiotic combination operates to reduce or inhibit the absorption of pathogens by the intestine by competitively inhibiting bacterial adherence or binding to intestinal enterocytes. The lactoferrin/polar lipid combination operates differently; lactoferrin binds to its intestinal receptors exerting its beneficial effects and inhibiting adsorption of pathogens to intestine. This mechanism of action of lactoferrin also enhances the binding of pathogens to the polar lipid rather than intestine thus directly or indirectly facilitating the decoying function of polar lipids. Thus, the combination of the two mechanisms can provide even more effective anti-pathogen activity than previously observed.

Thus, the combination of synergies found by including a combination of lactoferrin with prebiotics, the combination of lactoferrin with polar lipids, and the combination of polar lipids with prebiotics provide a nutritional composition with unique advantages for infants and children.

In addition to polar lipids, lactoferrin, prebiotics and LCPUFAs, the nutritional composition(s) of the disclosure may comprise at least one protein source, by which is meant excluding lactoferrin. The protein source can be any used in the art, e.g., nonfat milk, whey protein, casein, soy protein, hydrolyzed protein, amino acids, and the like. Bovine milk protein sources useful in practicing the present disclosure include, but are not limited to, milk protein powders, milk protein concentrates, milk protein isolates, nonfat milk solids, nonfat milk, nonfat dry milk, whey protein, whey protein isolates, whey protein concentrates, sweet whey, acid whey, casein, acid casein, caseinate (e.g. sodium caseinate, sodium calcium caseinate, calcium caseinate) and any combinations thereof.

In some embodiments, the proteins of the nutritional composition are provided as intact proteins. In other embodiments, the proteins are provided as a combination of both intact proteins and hydrolyzed proteins. In certain embodiments, the proteins may be partially hydrolyzed or extensively hydrolyzed. In still other embodiments, the protein source comprises amino acids. In yet another embodiment, the protein source may be supplemented with glutamine-containing peptides. In another embodiment, the protein component comprises extensively hydrolyzed protein. In still another embodiment, the protein component of the nutritional composition consists essentially of extensively hydrolyzed protein in order to minimize the occurrence of food allergy. In yet another embodiment, the protein source may be supplemented with glutamine-containing peptides.

Some people exhibit allergies or sensitivities to intact proteins, i.e. whole proteins, such as those in intact cow's milk protein or intact soy protein isolate-based formulas. Many of these people with protein allergies or sensitivities are able to tolerate hydrolyzed protein. Hydrolysate formulas (also referred to as semi-elemental formulas) contain protein that has been hydrolyzed or broken down into short peptide fragments and amino acids and as a result is more easily digested. In people with protein sensitivities or allergies, immune system associated allergies or sensitivities often result in cutaneous, respiratory or gastrointestinal symptoms such as vomiting and diarrhea. People who exhibit reactions to intact protein formulas often will not react to hydrolyzed protein formulas because their immune system does not recognize the hydrolyzed protein as the intact protein that causes their symptoms.

Some gliadins and bovine caseins may share epitopes recognized by anti-gliadin IgA antibodies. Accordingly, then, the nutritional composition of the present disclosure reduces the incidence of food allergy, such as, for example, protein allergies and, consequently, the immune reaction of some patients to proteins such as bovine casein, by providing a protein component comprising hydrolyzed proteins, such as hydrolyzed whey protein and/or hydrolyzed casein protein. A hydrolyzed protein component contains fewer allergenic epitopes than an intact protein component.

Accordingly, in some embodiments, the protein component of the nutritional composition comprises either partially or extensively hydrolyzed protein, such as protein from cow's milk. The hydrolyzed proteins may be treated with enzymes to break down some or most of the proteins that cause adverse symptoms with the goal of reducing allergic reactions, intolerance, and sensitization. Moreover, the proteins may be hydrolyzed by any method known in the art.

The terms "protein hydrolysates" or "hydrolyzed protein" are used interchangeably herein and refer to hydrolyzed proteins, wherein the degree of hydrolysis is may be from about 20% to about 80%, or from about 30% to about 80%, or even from about 40% to about 60%. The degree of hydrolysis is the extent to which peptide bonds are broken by a hydrolysis method. The degree of protein hydrolysis for purposes of characterizing the hydrolyzed protein component of the nutritional composition is easily determined by one of ordinary skill in the formulation arts by quantifying the amino nitrogen to total nitrogen ratio (AN/TN) of the protein component of the selected formulation. The amino nitrogen component is quantified by USP titration methods for determining amino nitrogen content, while the total nitrogen component is determined by the Tecator Kjeldahl method, all of which are well known methods to one of ordinary skill in the analytical chemistry art.

When a peptide bond in a protein is broken by enzymatic hydrolysis, one amino group is released for each peptide bond broken, causing an increase in amino nitrogen. It should be noted that even non-hydrolyzed protein would contain some exposed amino groups. Hydrolyzed proteins will also have a different molecular weight distribution than the non-hydrolyzed proteins from which they were formed. The functional and nutritional properties of hydrolyzed proteins can be affected by the different size peptides. A molecular weight profile is usually given by listing the percent by weight of particular ranges of molecular weight (in Daltons) fractions (e.g., 2,000 to 5,000 Daltons, greater than 5,000 Daltons).

As previously mentioned, persons who exhibit sensitivity to whole or intact proteins can benefit from consumption of nutritional formulas containing hydrolyzed proteins. Such sensitive persons may especially benefit from the consumption of a hypoallergenic formula.

In some embodiments, the nutritional composition of the present disclosure is substantially free of intact proteins. In this context, the term "substantially free" means that the preferred embodiments herein comprise sufficiently low concentrations of intact protein to thus render the formula hypoallergenic. The extent to which a nutritional composition in accordance with the disclosure is substantially free of intact proteins, and therefore hypoallergenic, is determined by the August 2000 Policy Statement of the American Academy of Pediatrics in which a hypoallergenic formula is defined as one which in appropriate clinical studies demonstrates that it does not provoke reactions in 90% of infants or children with confirmed cow's milk allergy with 95% confidence when given in prospective randomized, double-blind, placebo-controlled trials.

Another alternative for pediatric subjects, such as infants, that have food allergy and/or milk protein allergies is a protein-free nutritional composition based upon amino acids. Amino acids are the basic structural building units of protein. Breaking the proteins down to their basic chemical structure by completely pre-digesting the proteins makes amino acid-based formulas the most hypoallergenic formulas available.

In a particular embodiment, the nutritional composition is protein-free and contains free amino acids as a protein equivalent source. In this embodiment, the amino acids may comprise, but are not limited to, histidine, isoleucine, leucine, lysine, methionine, cysteine, phenylalanine, tyrosine, threonine, tryptophan, valine, alanine, arginine, asparagine, aspartic acid, glutamic acid, glutamine, glycine, proline, serine, carnitine, taurine and mixtures thereof. In some embodiments, the amino acids may be branched chain amino acids. In other embodiments, small amino acid peptides may be included as the protein component of the nutritional composition. Such small amino acid peptides may be naturally occurring or synthesized. The amount of free amino acids in the nutritional composition may vary from about 1 to about 5 g/100 kcal. In an embodiment, 100% of the free amino acids have a molecular weight of less than 500 Daltons. In this embodiment, the nutritional formulation may be hypoallergenic.

In a particular embodiment of the nutritional composition, the whey:casein ratio of the protein source is similar to that found in human breast milk. In an embodiment, the protein source comprises from about 40% to about 85% whey protein and from about 15% to about 60% casein.

In some embodiments, the nutritional composition comprises between about 1 g and about 7 g of a protein and/or protein equivalent source per 100 kcal. In other embodiments, the nutritional composition comprises between about 3.5 g and about 4.5 g of protein or protein equivalent per 100 kcal.

Moreover, the nutritional composition of the present disclosure may comprise at least one starch or starch component. A starch is a carbohydrate composed of two distinct polymer fractions: amylose and amylopectin. Amylose is the linear fraction consisting of α-1,4 linked glucose units. Amylopectin has the same structure as amylose, but some of the glucose units are combined in an α-1,6 linkage, giving rise to a branched structure. Starches generally contain 17-24% amylose and from 76-83% amylopectin. Yet special genetic varieties of plants have been developed that produce starch with unusual amylose to amylopectin ratios. Some plants produce starch that is free of amylose. These mutants produce starch granules in the endosperm and pollen that stain red with iodine and that contain nearly 100% amylopectin. Predominant among such amylopectin producing plants are waxy corn, waxy sorghum and waxy rice starch.

The performance of starches under conditions of heat, shear and acid may be modified or improved by chemical modifications. Modifications are usually attained by introduction of substituent chemical groups. For example, viscosity at high temperatures or high shear can be increased or stabilized by cross-linking with di- or polyfunctional reagents, such as phosphorus oxychloride.

In some instances, the nutritional compositions of the present disclosure comprise at least one starch that is gelatinized or pregelatinized. As is known in the art, gelatinization occurs when polymer molecules interact over a portion of their length to form a network that entraps solvent and/or solute molecules. Moreover, gels form when pectin molecules lose some water of hydration owing to competitive hydration of cosolute molecules. Factors that influence the occurrence of gelation include pH, concentration of cosolutes, concentration and type of cations, temperature and pectin concentration. Notably, LM pectin will gel only in the presence of divalent cations, such as calcium ions. And among LM pectins, those with the lowest degree of esterification have the highest gelling temperatures and the greatest need for divalent cations for crossbridging.

Meanwhile, pregelatinization of starch is a process of precooking starch to produce material that hydrates and swells in cold water. The precooked starch is then dried, for example by drum drying or spray drying. Moreover the starch of the present disclosure can be chemically modified to further extend the range of its finished properties. The nutritional compositions of the present disclosure may comprise at least one pregelatinized starch.

Native starch granules are insoluble in water, but, when heated in water, native starch granules begin to swell when sufficient heat energy is present to overcome the bonding forces of the starch molecules. With continued heating, the granule swells to many times its original volume. The friction between these swollen granules is the major factor that contributes to starch paste viscosity.

The nutritional composition of the present disclosure may comprise native or modified starches, such as, for example, waxy corn starch, waxy rice starch, corn starch, rice starch, potato starch, tapioca starch, wheat starch or any mixture thereof. Generally, common corn starch comprises about 25% amylose, while waxy corn starch is almost totally made up of amylopectin. Meanwhile, potato starch generally comprises about 20% amylose, rice starch comprises an amylose:amylopectin ratio of about 20:80, and waxy rice starch comprises only about 2% amylose. Further, tapioca starch generally comprises about 15% to about 18% amylose, and wheat starch has an amylose content of around 25%.

In some embodiments, the nutritional composition comprises gelatinized and/or pre-gelatinized waxy corn starch. In other embodiments, the nutritional composition comprises gelatinized and/or pre-gelatinized tapioca starch. Other gelatinized or pre-gelatinized starches, such as rice starch or potato starch may also be used.

Additionally, the nutritional compositions of the present disclosure comprise at least one source of pectin. The source of pectin may comprise any variety or grade of pectin known in the art. In some embodiments, the pectin has a degree of esterification of less than 50% and is classified as low methylated ("LM") pectin. In some embodiments, the pectin has a degree of esterification of greater than or equal to 50% and is classified as high-ester or high methylated ("HM") pectin. In still other embodiments, the pectin is very low ("VL") pectin, which has a degree of esterification that is less than approximately 15%. Further, the nutritional composition of the present disclosure may comprise LM pectin, HM pectin, VL pectin, or any mixture thereof. The nutritional composition may include pectin that is soluble in water. And, as known in the art, the solubility and viscosity of a pectin solution are related to the molecular weight, degree of esterification, concentration of the pectin preparation and the pH and presence of counterions.

Moreover, pectin has a unique ability to form gels. Generally, under similar conditions, a pectin's degree of gelation, the gelling temperature, and the gel strength are proportional to one another, and each is generally proportional to the molecular weight of the pectin and inversely proportional to the degree of esterification. For example, as the pH of a pectin solution is lowered, ionization of the carboxylate groups is repressed, and, as a result of losing their charge, saccharide molecules do not repel each other over their entire length. Accordingly, the polysaccharide molecules can associate over a portion of their length to form a gel. Yet pectins with increasing degrees of methylation will gel at somewhat higher pH because they have fewer carboxylate anions at any given pH. (J. N. Bemiller, *An Introduction to Pectins: Structure and Properties*, Chemistry and Function of Pectins; Chapter 1; 1986.)

The nutritional composition may comprise a gelatinized and/or pregelatinized starch together with pectin and/or gelatinized pectin. While not wishing to be bound by this or any other theory, it is believed that the use of pectin, such as LM pectin, which is a hydrocolloid of large molecular weight, together with starch granules, provides a synergistic effect that increases the molecular internal friction within a fluid matrix. The carboxylic groups of the pectin may also interact with calcium ions present in the nutritional composition, thus leading to an increase in viscosity, as the carboxylic groups of the pectin form a weak gel structure with the calcium ion(s), and also with peptides present in the nutritional composition. In some embodiments, the nutritional composition comprises a ratio of starch to pectin that is between about 12:1 and 20:1, respectively. In other embodiments, the ratio of starch to pectin is about 17:1. In some embodiments, the nutritional composition may comprise between about 0.05 and about 2.0% w/w pectin. In a particular embodiment, the nutritional composition may comprise about 0.5% w/w pectin.

Pectins for use herein typically have a peak molecular weight of 8,000 Daltons or greater. The pectins of the present disclosure have a preferred peak molecular weight of between 8,000 and about 500,000, more preferred is between about 10,000 and about 200,000 and most preferred is between about 15,000 and about 100,000 Daltons. In some embodiments, the pectin of the present disclosure may be hydrolyzed pectin. In certain embodiments, the nutritional composition comprises hydrolyzed pectin having a molecular weight less than that of intact or unmodified pectin. The hydrolyzed pectin of the present disclosure can be prepared by any means known in the art to reduce molecular weight. Examples of said means are chemical hydrolysis, enzymatic hydrolysis and mechanical shear. A preferred means of reducing the molecular weight is by alkaline or neutral hydrolysis at elevated temperature. In some embodiments, the nutritional composition comprises partially hydrolyzed pectin. In certain embodiments, the partially hydrolyzed pectin has a molecular weight that is less than that of intact or unmodified pectin but more than 3,300 Daltons.

The nutritional composition may contain at least one acidic polysaccharide. An acidic polysaccharide, such as negatively charged pectin, may induce an anti-adhesive effect on pathogens in a subject's gastrointestinal tract. Indeed, nonhuman milk acidic oligosaccharides derived from pectin are able to interact with the epithelial surface and are known to inhibit the adhesion of pathogens on the epithelial surface.

In some embodiments, the nutritional composition comprises at least one pectin-derived acidic oligosaccharide. Pectin-derived acidic oligosaccharide(s) (pAOS) result from enzymatic pectinolysis, and the size of a pAOS depends on the enzyme use and on the duration of the reaction. In such embodiments, the pAOS may beneficially affect a subject's stool viscosity, stool frequency, stool pH and/or feeding tolerance. The nutritional composition of the present disclosure may comprise between about 2 g pAOS per liter of formula and about 6 g pAOS per liter of formula. In an embodiment, the nutritional composition comprises about 0.2 g pAOS/dL, corresponding to the concentration of acidic oligosaccharides in human milk. (Fanaro et al., "Acidic Oligosaccharides from Pectin Hydrolysate as New Component for Infant Formulae: Effect on Intestinal Flora, Stool Characteristics, and pH", Journal of Pediatric Gastroenterology and Nutrition, 41: 186-190, August 2005)

In some embodiments, the nutritional composition comprises up to about 20% w/w of a mixture of starch and pectin. In some embodiments, the nutritional composition comprises up to about 19% starch and up to about 1% pectin. In other embodiments, the nutritional composition comprises about up to about 15% starch and up to about 5% pectin. In still other embodiments, the nutritional composition comprises up to about 18% starch and up to about 2% pectin. In some embodiments the nutritional composition comprises between about 0.05% w/w and about 20% w/w of a mixture of starch and pectin. Other embodiments include between about 0.05% and about 19% w/w starch and between about 0.05% and about 1% w/w pectin. Further, the nutritional composition may comprise between about 0.05% and about 15% w/w starch and between about 0.05% and about 5% w/w pectin.

In some embodiments, the nutritional composition comprises at least one additional carbohydrate source, that is, a carbohydrate component provided in addition to the aforementioned starch component. Additional carbohydrate sources can be any used in the art, e.g., lactose, glucose, fructose, corn syrup solids, maltodextrins, sucrose, starch, rice syrup solids, and the like. The amount of the additional carbohydrate component in the nutritional composition typically can vary from between about 5 g and about 25 g/100 kcal. In some embodiments, the amount of carbohydrate is between about 6 g and about 22 g/100 kcal. In other embodiments, the amount of carbohydrate is between about 12 g and about 14 g/100 kcal. In some embodiments, corn syrup solids are preferred. Moreover, hydrolyzed, partially hydrolyzed, and/or extensively hydrolyzed carbohydrates may be desirable for inclusion in the nutritional composition due to their easy digestibility. Specifically, hydrolyzed carbohydrates are less likely to contain allergenic epitopes.

Non-limiting examples of carbohydrate materials suitable for use herein include hydrolyzed or intact, naturally or chemically modified, starches sourced from corn, tapioca, rice or potato, in waxy or non-waxy forms. Non-limiting examples of suitable carbohydrates include various hydrolyzed starches characterized as hydrolyzed cornstarch, maltodextrin, maltose, corn syrup, dextrose, corn syrup solids, glucose, and various other glucose polymers and combinations thereof. Non-limiting examples of other suitable carbohydrates include those often referred to as sucrose, lactose, fructose, high fructose corn syrup, indigestible oligosaccharides such as fructooligosaccharides and combinations thereof.

In one particular embodiment, the additional carbohydrate component of the nutritional composition is comprised of 100% lactose. In another embodiment, the additional carbohydrate component comprises between about 0% and 60% lactose. In another embodiment, the additional carbohydrate component comprises between about 15% and 55% lactose. In yet another embodiment, the additional carbohydrate component comprises between about 20% and 30% lactose. In these embodiments, the remaining source of carbohydrates may be any carbohydrate known in the art. In an embodiment, the carbohydrate component comprises about 25% lactose and about 75% corn syrup solids.

In some embodiments the nutritional composition comprises sialic acid. Sialic acids are a family of over 50 members of 9-carbon sugars, all of which are derivatives of neuroaminic acid. The predominant sialic acid family found in humans is from the N-acetylneuraminic acid sub-family. Sialic acids are found in milk, such as bovine and caprine.

In mammals, neuronal cell membranes have the highest concentration of sialic acid compared to other body cell membranes. Sialic acid residues are also components of gangliosides.

If included in the nutritional composition, sialic acid may be present in an amount from about 0.5 mg/100 kcals to about 45 mg/100 kcal. In some embodiments sialic acid may be present in an amount from about 5 mg/100 kcals to about 30 mg/100 kcals. In still other embodiments, sialic acid may be present in an amount from about 10 mg/100 kcals to about 25 mg/100 kcals.

In one embodiment, the nutritional composition may contain one or more probiotics. Any probiotic known in the art may be acceptable in this embodiment. In a particular embodiment, the probiotic may be selected from any *Lactobacillus* species, *Lactobacillus rhamnosus* GG (ATCC number 53103), *Bifidobacterium* species, *Bifidobacterium longum* BB536 (BL999, ATCC: BAA-999), *Bifidobacterium longum* AH1206 (NCIMB: 41382), *Bifidobacterium breve* AH1205 (NCIMB: 41387), *Bifidobacterium infantis* 35624 (NCIMB: 41003), and *Bifidobacterium animalis* subsp. *lactis* BB-12 (DSM No. 10140) or any combination thereof.

If included in the composition, the amount of the probiotic may vary from about $1 \times 10^4$ to about $1.5 \times 10^{12}$ cfu of probiotic(s) per 100 kcal. In some embodiments the amount of probiotic may be from about $1 \times 10^6$ to about $1 \times 10^9$ cfu of probiotic(s) per 100 kcal. In certain other embodiments the amount of probitic may vary from about $1 \times 10^7$ cfu/100 kcal to about $1 \times 10^8$ cfu of probiotic(s) per 100 kcal.

In an embodiment, the probiotic(s) may be viable or non-viable. As used herein, the term "viable", refers to live microorganisms. The term "non-viable" or "non-viable probiotic" means non-living probiotic microorganisms, their cellular components and/or metabolites thereof. Such non-viable probiotics may have been heat-killed or otherwise inactivated, but they retain the ability to favorably influence the health of the host. The probiotics useful in the present disclosure may be naturally-occurring, synthetic or developed through the genetic manipulation of organisms, whether such source is now known or later developed.

In some embodiments, the nutritional composition may include a source comprising probiotic cell equivalents, which refers to the level of non-viable, non-replicating probiotics equivalent to an equal number of viable cells. The term "non-replicating" is to be understood as the amount of non-replicating microorganisms obtained from the same amount of replicating bacteria (cfu/g), including inactivated probiotics, fragments of DNA, cell wall or cytoplasmic compounds. In other words, the quantity of non-living, non-replicating organisms is expressed in terms of cfu as if all the microorganisms were alive, regardless whether they are dead, non-replicating, inactivated, fragmented etc. In non-viable probiotics are included in the nutritional composition, the amount of the probiotic cell equivalents may vary from about $1 \times 10^4$ to about $1.5 \times 10^{10}$ cell equivalents of probiotic(s) per 100 kcal. In some embodiments the amount of probiotic cell equivalents may be from about $1 \times 10^6$ to about $1 \times 10^9$ cell equivalents of probiotic(s) per 100 kcal nutritional composition. In certain other embodiments the amount of probiotic cell equivalents may vary from about $1 \times 10^7$ to about $1 \times 10^8$ cell equivalents of probiotic(s) per 100 kcal of nutritional composition.

In some embodiments, the probiotic source incorporated into the nutritional composition may comprise both viable colony-forming units, and non-viable cell-equivalents.

In some embodiments, the nutritional composition includes a culture supernatant from a late-exponential growth phase of a probiotic batch-cultivation process. Without wishing to be bound by theory, it is believed that the activity of the culture supernatant can be attributed to the mixture of components (including proteinaceous materials, and possibly including (exo)polysaccharide materials) as found released into the culture medium at a late stage of the exponential (or "log") phase of batch cultivation of the probiotic. The term "culture supernatant" as used herein, includes the mixture of components found in the culture medium. The stages recognized in batch cultivation of bacteria are known to the skilled person. These are the "lag," the "log" ("logarithmic" or "exponential"), the "stationary" and the "death" (or "logarithmic decline") phases. In all phases during which live bacteria are present, the bacteria metabolize nutrients from the media, and secrete (exert, release) materials into the culture medium. The composition of the secreted material at a given point in time of the growth stages is not generally predictable.

In an embodiment, a culture supernatant is obtainable by a process comprising the steps of (a) subjecting a probiotic such as LGG to cultivation in a suitable culture medium using a batch process; (b) harvesting the culture supernatant at a late exponential growth phase of the cultivation step, which phase is defined with reference to the second half of the time between the lag phase and the stationary phase of the batch-cultivation process; (c) optionally removing low molecular weight constituents from the supernatant so as to retain molecular weight constituents above 5-6 kiloDaltons (kDa); (d) removing liquid contents from the culture supernatant so as to obtain the composition.

The culture supernatant may comprise secreted materials that are harvested from a late exponential phase. The late exponential phase occurs in time after the mid exponential phase (which is halftime of the duration of the exponential phase, hence the reference to the late exponential phase as being the second half of the time between the lag phase and the stationary phase). In particular, the term "late exponential phase" is used herein with reference to the latter quarter portion of the time between the lag phase and the stationary phase of the LGG batch-cultivation process. In some embodiments, the culture supernatant is harvested at a point in time of 75% to 85% of the duration of the exponential phase, and may be harvested at about ⅚ of the time elapsed in the exponential phase.

As noted, the disclosed nutritional composition may comprise a source of β-glucan. Glucans are polysaccharides, specifically polymers of glucose, which are naturally occurring and may be found in cell walls of bacteria, yeast, fungi, and plants. Beta glucans (β-glucans) are themselves a diverse subset of glucose polymers, which are made up of chains of glucose monomers linked together via beta-type glycosidic bonds to form complex carbohydrates.

β-1,3-glucans are carbohydrate polymers purified from, for example, yeast, mushroom, bacteria, algae, or cereals. (Stone B A, Clarke A E. Chemistry and Biology of (1-3)-Beta-Glucans. London:Portland Press Ltd; 1993.) The chemical structure of β-1,3-glucan depends on the source of the β-1,3-glucan. Moreover, various physiochemical parameters, such as solubility, primary structure, molecular weight, and branching, play a role in biological activities of β-1,3-glucans. (Yadomae T., Structure and biological activities of fungal beta-1,3-glucans. Yakugaku Zasshi. 2000; 120:413-431.)

β-1,3-glucans are naturally occurring polysaccharides, with or without β-1,6-glucose side chains that are found in the cell walls of a variety of plants, yeasts, fungi and bacteria. β-1,3;1,6-glucans are those containing glucose units with (1,3) links having side chains attached at the (1,6) position(s). β-1,3;1,6 glucans are a heterogeneous group of glucose polymers that share structural commonalties, including a backbone of straight chain glucose units linked by a β-1,3 bond with β-1,6-linked glucose branches extending from this backbone. While this is the basic structure for the presently described class of β-glucans, some variations may exist. For example, certain yeast β-glucans have additional regions of β(1,3) branching extending from the β(1,6) branches, which add further complexity to their respective structures.

β-glucans derived from baker's yeast, Saccharomyces cerevisiae, are made up of chains of D-glucose molecules connected at the 1 and 3 positions, having side chains of glucose attached at the 1 and 6 positions. Yeast-derived β-glucan is an insoluble, fiber-like, complex sugar having the general structure of a linear chain of glucose units with a β-1,3 backbone interspersed with β-1,6 side chains that are generally 6-8 glucose units in length. More specifically, β-glucan derived from baker's yeast is poly-(1,6)-β-D-glucopyranosyl-(1,3)-β-D-glucopyranose.

Furthermore, β-glucans are well tolerated and do not produce or cause excess gas, abdominal distension, bloating or diarrhea in pediatric subjects. Addition of β-glucan to a nutritional composition for a pediatric subject, such as an infant formula, a growing-up milk or another children's nutritional product, will improve the subject's immune response by increasing resistance against invading pathogens and therefore maintaining or improving overall health.

The nutritional composition of the present disclosure comprises β-glucan. In some embodiments, the β-glucan is β-1,3;1,6-glucan. In some embodiments, the β-1,3;1,6-glucan is derived from baker's yeast. The nutritional composition may comprise whole glucan particle β-glucan, particulate β-glucan, PGG-glucan (poly-1,6-β-D-glucopyranosyl-1,3-β-D-glucopyranose) or any mixture thereof.

In some embodiments, the amount of β-glucan present in the composition is at between about 0.010 and about 0.080 g per 100 g of composition. In other embodiments, the nutritional composition comprises between about 10 and about 30 mg β-glucan per serving. In another embodiment, the nutritional composition comprises between about 5 and about 30 mg β-glucan per 8 fl. oz. (236.6 mL) serving. In other embodiments, the nutritional composition comprises an amount of β-glucan sufficient to provide between about 15 mg and about 90 mg β-glucan per day. The nutritional composition may be delivered in multiple doses to reach a target amount of β-glucan delivered to the subject throughout the day.

In some embodiments, the amount of β-glucan in the nutritional composition is between about 3 mg and about 17 mg per 100 kcal. In another embodiment the amount of β-glucan is between about 6 mg and about 17 mg per 100 kcal.

One or more vitamins and/or minerals may also be added in to the nutritional composition in amounts sufficient to supply the daily nutritional requirements of a subject. It is to be understood by one of ordinary skill in the art that vitamin and mineral requirements will vary, for example, based on the age of the child. For instance, an infant may have different vitamin and mineral requirements than a child between the ages of one and thirteen years. Thus, the embodiments are not intended to limit the nutritional composition to a particular age group but, rather, to provide a range of acceptable vitamin and mineral components.

The nutritional composition may optionally include, but is not limited to, one or more of the following vitamins or derivations thereof: vitamin $B_1$ (thiamin, thiamin pyrophosphate, TPP, thiamin triphosphate, TTP, thiamin hydrochloride, thiamin mononitrate), vitamin $B_2$ (riboflavin, flavin mononucleotide, FMN, flavin adenine dinucleotide, FAD, lactoflavin, ovoflavin), vitamin $B_3$ (niacin, nicotinic acid, nicotinamide, niacinamide, nicotinamide adenine dinucleotide, NAD, nicotinic acid mononucleotide, NicMN, pyridine-3-carboxylic acid), vitamin $B_3$-precursor tryptophan, vitamin $B_6$ (pyridoxine, pyridoxal, pyridoxamine, pyridoxine hydrochloride), pantothenic acid (pantothenate, panthenol), folate (folic acid, folacin, pteroylglutamic acid), vitamin $B_{12}$ (cobalamin, methylcobalamin, deoxyadenosylcobalamin, cyanocobalamin, hydroxycobalamin, adenosylcobalamin), biotin, vitamin C (ascorbic acid), vitamin A (retinol, retinyl acetate, retinyl palmitate, retinyl esters with other long-chain fatty acids, retinal, retinoic acid, retinol esters), vitamin D (calciferol, cholecalciferol, vitamin $D_3$, 1,25,-dihydroxyvitamin D), vitamin E ($\alpha$-tocopherol, $\alpha$-tocopherol acetate, $\alpha$-tocopherol succinate, $\alpha$-tocopherol nicotinate, $\alpha$-tocopherol), vitamin K (vitamin $K_1$, phylloquinone, naphthoquinone, vitamin $K_2$, menaquinone-7, vitamin $K_3$, menaquinone-4, menadione, menaquinone-8, menaquinone-8H, menaquinone-9, menaquinone-9H, menaquinone-10, menaquinone-11, menaquinone-12, menaquinone-13), choline, inositol, $\beta$-carotene and any combinations thereof.

Further, the nutritional composition may optionally include, but is not limited to, one or more of the following minerals or derivations thereof: boron, calcium, calcium acetate, calcium gluconate, calcium chloride, calcium lactate, calcium phosphate, calcium sulfate, chloride, chromium, chromium chloride, chromium picolonate, copper, copper sulfate, copper gluconate, cupric sulfate, fluoride, iron, carbonyl iron, ferric iron, ferrous fumarate, ferric orthophosphate, iron trituration, polysaccharide iron, iodide, iodine, magnesium, magnesium carbonate, magnesium hydroxide, magnesium oxide, magnesium stearate, magnesium sulfate, manganese, molybdenum, phosphorus, potassium, potassium phosphate, potassium iodide, potassium chloride, potassium acetate, selenium, sulfur, sodium, docusate sodium, sodium chloride, sodium selenate, sodium molybdate, zinc, zinc oxide, zinc sulfate and mixtures thereof. Non-limiting exemplary derivatives of mineral compounds include salts, alkaline salts, esters and chelates of any mineral compound.

The minerals can be added to nutritional compositions in the form of salts such as calcium phosphate, calcium glycerol phosphate, sodium citrate, potassium chloride, potassium phosphate, magnesium phosphate, ferrous sulfate, zinc sulfate, cupric sulfate, manganese sulfate, and sodium selenite. Additional vitamins and minerals can be added as known within the art.

In an embodiment, the nutritional composition may contain between about 10 and about 50% of the maximum dietary recommendation for any given country, or between about 10 and about 50% of the average dietary recommendation for a group of countries, per serving of vitamins A, C, and E, zinc, iron, iodine, selenium, and choline. In another embodiment, the children's nutritional composition may supply about 10-30% of the maximum dietary recommendation for any given country, or about 10-30% of the average dietary recommendation for a group of countries, per serving of B-vitamins. In yet another embodiment, the levels of vitamin D, calcium, magnesium, phosphorus, and potassium in the children's nutritional product may correspond with the average levels found in milk. In other embodiments, other nutrients in the children's nutritional composition may be present at about 20% of the maximum dietary recommendation for any given country, or about 20% of the average dietary recommendation for a group of countries, per serving.

The nutritional compositions of the present disclosure may optionally include one or more of the following flavoring agents, including, but not limited to, flavored extracts, volatile oils, cocoa or chocolate flavorings, peanut butter flavoring, cookie crumbs, vanilla or any commercially available flavoring. Examples of useful flavorings include, but are not limited to, pure anise extract, imitation banana extract, imitation cherry extract, chocolate extract, pure lemon extract, pure orange extract, pure peppermint extract, honey, imitation pineapple extract, imitation rum extract, imitation strawberry extract, or vanilla extract; or volatile oils, such as balm oil, bay oil, bergamot oil, cedarwood oil, cherry oil, cinnamon oil, clove oil, or peppermint oil; peanut butter, chocolate flavoring, vanilla cookie crumb, butterscotch, toffee, and mixtures thereof. The amounts of flavoring agent can vary greatly depending upon the flavoring agent used. The type and amount of flavoring agent can be selected as is known in the art.

The nutritional compositions of the present disclosure may optionally include one or more emulsifiers that may be added for stability of the final product. Examples of suitable emulsifiers include, but are not limited to, lecithin (e.g., from egg or soy), alpha lactalbumin and/or mono- and di-glycerides, and mixtures thereof. Other emulsifiers are readily apparent to the skilled artisan and selection of suitable emulsifier(s) will depend, in part, upon the formulation and final product.

The nutritional compositions of the present disclosure may optionally include one or more preservatives that may also be added to extend product shelf life. Suitable preservatives include, but are not limited to, potassium sorbate, sodium sorbate, potassium benzoate, sodium benzoate, calcium disodium EDTA, and mixtures thereof.

The nutritional compositions of the present disclosure may optionally include one or more stabilizers. Suitable stabilizers for use in practicing the nutritional composition of the present disclosure include, but are not limited to, gum arabic, gum ghatti, gum karaya, gum tragacanth, agar, furcellaran, guar gum, gellan gum, locust bean gum, pectin, low methoxyl pectin, gelatin, microcrystalline cellulose, CMC (sodium carboxymethylcellulose), methylcellulose hydroxypropyl methyl cellulose, hydroxypropyl cellulose, DATEM (diacetyl tartaric acid esters of mono- and diglycerides), dextran, carrageenans, and mixtures thereof.

The disclosed nutritional composition(s) may be provided in any form known in the art, such as a powder, a gel, a suspension, a paste, a solid, a liquid, a liquid concentrate, a reconstituteable powdered milk substitute or a ready-to-use product. The nutritional composition may, in certain embodiments, comprise a nutritional supplement, children's nutritional product, infant formula, human milk fortifier, growing-up milk or any other nutritional composition designed for an infant or a pediatric subject. Nutritional compositions of the present disclosure include, for example, orally-ingestible, health-promoting substances including, for example, foods, beverages, tablets, capsules and powders. Moreover, the nutritional composition of the present disclosure may be standardized to a specific caloric content, it may be provided as a ready-to-use product, or it may be provided in a concentrated form. In some embodiments, the nutritional composition is in powder form with a particle size in the range of 5 μm to 1500 μm, more preferably in the range of 10 μm to 300 μm.

If the nutritional composition is in the form of a ready-to-use product, the osmolality of the nutritional composition may be between about 100 and about 1100 mOsm/kg water, more typically about 200 to about 700 mOsm/kg water.

Suitable fat or lipid sources for the nutritional composition of the present disclosure may be any known or used in the art, including but not limited to, animal sources, e.g., milk fat, butter, butter fat, egg yolk lipid; marine sources, such as fish oils, marine oils, single cell oils; vegetable and plant oils, such as corn oil, canola oil, sunflower oil, soybean oil, palm olein oil, coconut oil, high oleic sunflower oil, evening primrose oil, rapeseed oil, olive oil, flaxseed (linseed) oil, cottonseed oil, high oleic safflower oil, palm stearin, palm kernel oil, wheat germ oil; medium chain triglyceride oils and emulsions and esters of fatty acids; and any combinations thereof.

The nutritional compositions of the disclosure may provide minimal, partial or total nutritional support. The compositions may be nutritional supplements or meal replacements. The compositions may, but need not, be nutritionally complete. In an embodiment, the nutritional composition of the disclosure is nutritionally complete and contains suitable types and amounts of lipid, carbohydrate, protein, vitamins and minerals. The amount of lipid or fat typically can vary from about 1 to about 7 g/100 kcal. The amount of protein typically can vary from about 1 to about 7 g/100 kcal. The amount of carbohydrate typically can vary from about 6 to about 22 g/100 kcal.

The nutritional composition of the present disclosure may further include at least one additional phytonutrient, that is, another phytonutrient component in addition to the pectin and/or starch components described hereinabove. Phytonutrients, or their derivatives, conjugated forms or precursors, that are identified in human milk are preferred for inclusion in the nutritional composition. Typically, dietary sources of carotenoids and polyphenols are absorbed by a nursing mother and retained in milk, making them available to nursing infants. Addition of these phytonutrients to infant or children's formulas allows such formulas to mirror the composition and functionality of human milk and to promote general health and well being.

For example, in some embodiments, the nutritional composition of the present disclosure may comprise, in an 8 fl. oz. (236.6 mL) serving, between about 80 and about 300 mg anthocyanins, between about 100 and about 600 mg proanthocyanidins, between about 50 and about 500 mg flavan-3-ols, or any combination or mixture thereof. In other embodiments, the nutritional composition comprises apple extract, grape seed extract, or a combination or mixture thereof. Further, the at least one phytonutrient of the nutritional composition may be derived from any single or blend of fruit, grape seed and/or apple or tea extract(s).

For the purposes of this disclosure, additional phytonutrients may be added to a nutritional composition in native, purified, encapsulated and/or chemically or enzymatically-modified form so as to deliver the desired sensory and stability properties. In the case of encapsulation, it is desirable that the encapsulated phytonutrients resist dissolution with water but are released upon reaching the small intestine. This could be achieved by the application of enteric coatings, such as cross-linked alginate and others.

Examples of additional phytonutrients suitable for the nutritional composition include, but are not limited to, anthocyanins, proanthocyanidins, flavan-3-ols (i.e. catechins, epicatechins, etc.), flavanones, flavonoids, isoflavonoids, stilbenoids (i.e. resveratrol, etc.) proanthocyanidins, anthocyanins, resveratrol, quercetin, curcumin, and/or any mixture thereof, as well as any possible combination of phytonutrients in a purified or natural form. Certain components, especially plant-based components of the nutritional compositions may provide a source of phytonutrients.

Some amounts of phytonutrients may be inherently present in known ingredients, such as natural oils, that are commonly used to make nutritional compositions for pediatric subjects. These inherent phytonutrient(s) may be but are not necessarily considered part of the phytonutrient component described in the present disclosure. In some embodiments, the phytonutrient concentrations and ratios as described herein are calculated based upon added and inherent phytonutrient sources. In other embodiments, the phytonutrient concentrations and ratios as described herein are calculated based only upon added phytonutrient sources.

In some embodiments, the nutritional composition comprises anthocyanins, such as, for example, glucosides of aurantinidin, cyanidin, delphinidin, europinidin, luteolinidin, pelargonidin, malvidin, peonidin, petunidin, and rosinidin. These and other anthocyanins suitable for use in the nutritional composition are found in a variety of plant sources. Anthocyanins may be derived from a single plant source or a combination of plant sources. Non-limiting examples of plants rich in anthocyanins suitable for use in the inventive composition include: berries (acai, grape, bilberry, blueberry, lingonberry, black currant, chokeberry, blackberry, raspberry, cherry, red currant, cranberry, crowberry, cloudberry, whortleberry, rowanberry), purple corn, purple potato, purple carrot, red sweet potato, red cabbage, eggplant.

In some embodiments, the nutritional composition of the present disclosure comprises proanthocyanidins, which include but are not limited to flavan-3-ols and polymers of flavan-3-ols (e.g., catechins, epicatechins) with degrees of polymerization in the range of 2 to 11. Such compounds may be derived from a single plant source or a combination of plant sources. Non-limiting examples of plant sources rich in proanthocyanidins suitable for use in the inventive nutritional composition include: grape, grape skin, grape seed, green tea, black tea, apple, pine bark, cinnamon, cocoa, bilberry, cranberry, black currant chokeberry.

Non-limiting examples of flavan-3-ols which are suitable for use in the inventive nutritional composition include catechin, epicatechin, gallocatechin, epigallocatechin, epicatechin gallate, epicatechin-3-gallate, epigallocatechin and gallate. Plants rich in the suitable flavan-3-ols include, but are not limited to, teas, red grapes, cocoa, green tea, apricot and apple.

Certain polyphenol compounds, in particular flavan-3-ols, may improve learning and memory in a human subject by increasing brain blood flow, which is associated with an increase and sustained brain energy/nutrient delivery as well as formation of new neurons. Polyphenols may also provide neuroprotective actions and may increase both brain synaptogenesis and antioxidant capability, thereby supporting optimal brain development in younger children.

Preferred sources of flavan-3-ols for the nutritional composition include at least one apple extract, at least one grape seed extract or a mixture thereof. For apple extracts, flavan-3-ols are broken down into monomers occurring in the range 4% to 20% and polymers in the range 80% to 96%. For grape seed extracts flavan-3-ols are broken down into monomers (about 46%) and polymers (about 54%) of the total flavan-3-ols and total polyphenolic content. Preferred degree of polymerization of polymeric flavan-3-ols is in the range of between about 2 and 11. Furthermore, apple and grape seed extracts may contain catechin, epicatechin, epigallocatechin, epicatechin gallate, epigallocatechin gallate, polymeric proanthocyanidins, stilbenoids (i.e. resveratrol), flavonols (i.e. quercetin, myricetin), or any mixture thereof. Plant sources rich in flavan-3-ols include, but are not limited to apple, grape seed, grape, grape skin, tea (green or black), pine bark, cinnamon, cocoa, bilberry, cranberry, black currant, chokeberry.

If the nutritional composition is administered to a pediatric subject, an amount of flavan-3-ols, including monomeric flavan-3-ols, polymeric flavan-3-ols or a combination thereof, ranging from between about 0.01 mg and about 450 mg per day may be administered. In some cases, the amount of flavan-3-ols administered to an infant or child may range from about 0.01 mg to about 170 mg per day, from about 50 to about 450 mg per day, or from about 100 mg to about 300 mg per day.

In an embodiment of the disclosure, flavan-3-ols are present in the nutritional composition in an amount ranging from about 0.4 to about 3.8 mg/g nutritional composition (about 9 to about 90 mg/100 kcal). In another embodiment, flavan-3-ols are present in an amount ranging from about 0.8 to about 2.5 mg/g nutritional composition (about 20 to about 60 mg/100 kcal).

In some embodiments, the nutritional composition of the present disclosure comprises flavanones. Non-limiting examples of suitable flavanones include butin, eriodictyol, hesperetin, hesperidin, homeriodictyol, isosakuranetin, naringenin, naringin, pinocembrin, poncirin, sakuranetin, sakuranin, steurbin. Plant sources rich in flavanones include, but are not limited to orange, tangerine, grapefruit, lemon, lime. The nutritional composition may be formulated to deliver between about 0.01 and about 150 mg flavanones per day.

Moreover, the nutritional composition may also comprise flavonols. Flavonols from plant or algae extracts may be used. Flavonols, such as ishrhametin, kaempferol, myricetin, quercetin, may be included in the nutritional composition in amounts sufficient to deliver between about 0.01 and 150 mg per day to a subject.

The phytonutrient component of the nutritional composition may also comprise phytonutrients that have been identified in human milk, including but not limited to naringenin, hesperetin, anthocyanins, quercetin, kaempferol, epicatechin, epigallocatechin, epicatechin-gallate, epigallocatechin-gallate or any combination thereof. In certain embodiments, the nutritional composition comprises between about 50 and about 2000 nmol/L epicatechin, between about 40 and about 2000 nmol/L epicatechin gallate, between about 100 and about 4000 nmol/L epigallocatechin gallate, between about 50 and about 2000 nmol/L naringenin, between about 5 and about 500 nmol/L kaempferol, between about 40 and about 4000 nmol/L hesperetin, between about 25 and about 2000 nmol/L anthocyanins, between about 25 and about 500 nmol/L quercetin, or a mixture thereof. Furthermore, the nutritional composition may comprise the metabolite(s) of a phytonutrient or of its parent compound, or it may comprise other classes of dietary phytonutrients, such as glucosinolate or sulforaphane.

In certain embodiments, the nutritional composition comprises carotenoids, such as lutein, zeaxanthin, astaxanthin, lycopene, beta-carotene, alpha-carotene, gamma-carotene, and/or beta-cryptoxanthin. Plant sources rich in carotenoids include, but are not limited to kiwi, grapes, citrus, tomatoes, watermelons, papayas and other red fruits, or dark greens, such as kale, spinach, turnip greens, collard greens, romaine lettuce, broccoli, zucchini, garden peas and Brussels sprouts, spinach, carrots.

Humans cannot synthesize carotenoids, but over 34 carotenoids have been identified in human breast milk, including isomers and metabolites of certain carotenoids. In addition to their presence in breast milk, dietary carotenoids, such as alpha and beta-carotene, lycopene, lutein, zeaxanthin, astaxanthin, and cryptoxanthin are present in serum of lactating women and breastfed infants. Carotenoids in general have been reported to improve cell-to-cell communication, promote immune function, support healthy respiratory health, protect skin from UV light damage, and have been linked to reduced risk of certain types of cancer, and all-cause mortality. Furthermore, dietary sources of carotenoids and/or polyphenols are absorbed by human subjects, accumulated and retained in breast milk, making them available to nursing infants. Thus, addition of phytonutrients to infant formulas or children's products would bring the formulas closer in composition and functionality to human milk.

Flavonoids, as a whole, may also be included in the nutritional composition, as flavonoids cannot be synthesized by humans. Moreover, flavonoids from plant or algae extracts may be useful in the monomer, dimer and/or polymer forms. In some embodiments, the nutritional composition comprises levels of the monomeric forms of flavonoids similar to those in human milk during the first three months of lactation. Although flavonoid aglycones (monomers) have been identified in human milk samples, the conjugated forms of flavonoids and/or their metabolites may also be useful in the nutritional composition. The flavonoids could be added in the following forms: free, glucuronides, methyl glucuronides, sulphates, and methyl sulphates.

The nutritional composition may also comprise isoflavonoids and/or isoflavones. Examples include, but are not limited to, genistein (genistin), daidzein (daidzin), glycitein, biochanin A, formononetin, coumestrol, irilone, orobol, pseudobaptigenin, anagyroidisoflavone A and B, calycosin, glycitein, irigenin, 5-O-methylgenistein, pratensein, prunetin, psi-tectorigenin, retusin, tectorigenin, iridin, ononin, puerarin, tectoridin, derrubone, luteone, wighteone, alpinumisoflavone, barbigerone, di-O-methylalpinumisoflavone, and 4'-methyl-alpinumisoflavone. Plant sources rich in isoflavonoids, include, but are not limited to, soybeans, psoralea, kudzu, lupine, fava, chick pea, alfalfa, legumes and peanuts. The nutritional composition may be formulated to deliver between about 0.01 and about 150 mg isoflavones and/or isoflavonoids per day.

In an embodiment, the nutritional composition(s) of the present disclosure comprises an effective amount of choline. Choline is a nutrient that is essential for normal function of cells. It is a precursor for membrane phospholipids, and it accelerates the synthesis and release of acetylcholine, a neurotransmitter involved in memory storage. Moreover, though not wishing to be bound by this or any other theory, it is believed that dietary choline and docosahexaenoic acid (DHA) act synergistically to promote the biosynthesis of phosphatidylcholine and thus help promote synaptogenesis in human subjects. Additionally, choline and DHA may exhibit the synergistic effect of promoting dendritic spine formation, which is important in the maintenance of established synaptic connections. In some embodiments, the nutritional composition(s) of the present disclosure includes an effective amount of choline, which is about 20 mg choline per 8 fl. oz. (236.6 mL) serving to about 100 mg per 8 fl. oz. (236.6 mL) serving.

Moreover, in some embodiments, the nutritional composition is nutritionally complete, containing suitable types and amounts of lipids, carbohydrates, proteins, vitamins and minerals to be a subject's sole source of nutrition. Indeed, the nutritional composition may optionally include any number of proteins, peptides, amino acids, fatty acids, probiotics and/or their metabolic by-products, prebiotics, carbohydrates and any other nutrient or other compound that may provide many nutritional and physiological benefits to a subject. Further, the nutritional composition of the present disclosure may comprise flavors, flavor enhancers, sweeteners, pigments, vitamins, minerals, therapeutic ingredients, functional food ingredients, food ingredients, processing ingredients or combinations thereof.

The present disclosure further provides a method for providing nutritional support to a subject. The method includes administering to the subject an effective amount of the nutritional composition of the present disclosure.

The nutritional composition may be expelled directly into a subject's intestinal tract. In some embodiments, the nutritional composition is expelled directly into the gut. In some embodiments, the composition may be formulated to be consumed or administered enterally under the supervision of a physician and may be intended for the specific dietary management of a disease or condition, such as celiac disease and/or food allergy, for which distinctive nutritional requirements, based on recognized scientific principles, are established by medical evaluation.

The nutritional composition of the present disclosure is not limited to compositions comprising nutrients specifically listed herein. Any nutrients may be delivered as part of the composition for the purpose of meeting nutritional needs and/or in order to optimize the nutritional status in a subject.

In some embodiments, the nutritional composition may be delivered to an infant from birth until a time that matches full-term gestation. In some embodiments, the nutritional composition may be delivered to an infant until at least about three months corrected age. In another embodiment, the nutritional composition may be delivered to a subject as long as is necessary to correct nutritional deficiencies. In yet another embodiment, the nutritional composition may be delivered to an infant from birth until at least about six months corrected age. In yet another embodiment, the nutritional composition may be delivered to an infant from birth until at least about one year corrected age.

The nutritional composition of the present disclosure may be standardized to a specific caloric content, it may be provided as a ready-to-use product, or it may be provided in a concentrated form.

In some embodiments, the nutritional composition of the present disclosure is a growing-up milk. Growing-up milks are fortified milk-based beverages intended for children over 1 year of age (typically from 1-3 years of age, from 4-6 years of age or from 1-6 years of age). They are not medical foods and are not intended as a meal replacement or a supplement to address a particular nutritional deficiency. Instead, growing-up milks are designed with the intent to serve as a complement to a diverse diet to provide additional insurance that a child achieves continual, daily intake of all essential vitamins and minerals, macronutrients plus additional functional dietary components, such as non-essential nutrients that have purported health-promoting properties.

The exact composition of a nutritional composition according to the present disclosure can vary from market-to-market, depending on local regulations and dietary intake information of the population of interest. In some embodiments, nutritional compositions according to the disclosure consist of a milk protein source, such as whole or skim milk, plus added sugar and sweeteners to achieve desired sensory properties, and added vitamins and minerals. The fat composition is typically derived from the milk raw materials. Total protein can be targeted to match that of human milk, cow milk or a lower value. Total carbohydrate is usually targeted to provide as little added sugar, such as sucrose or fructose, as possible to achieve an acceptable taste. Typically, Vitamin A, calcium and Vitamin D are added at levels to match the nutrient contribution of regional cow milk. Otherwise, in some embodiments, vitamins and minerals can be added at levels that provide approximately 20% of the dietary reference intake (DRI) or 20% of the Daily Value (DV) per serving. Moreover, nutrient values can vary between markets depending on the identified nutritional needs of the intended population, raw material contributions and regional regulations.

In certain embodiments, the nutritional composition is hypoallergenic. In other embodiments, the nutritional composition is kosher. In still further embodiments, the nutritional composition is a non-genetically modified product. In an embodiment, the nutritional formulation is sucrose-free. The nutritional composition may also be lactose-free. In other embodiments, the nutritional composition does not contain any medium-chain triglyceride oil. In some embodiments, no carrageenan is present in the composition. In other embodiments, the nutritional composition is free of all gums.

In some embodiments, the disclosure is directed to a staged nutritional feeding regimen for a pediatric subject, such as an infant or child, which includes a plurality of different nutritional compositions according to the present disclosure. Each nutritional composition comprises a hydrolyzed protein, at least one pre-gelatinized starch, and at least one pectin. In certain embodiments, the nutritional compositions of the feeding regimen may also include a source of long chain polyunsaturated fatty acid, at least one prebiotic, an iron source, a source of β-glucan, vitamins or minerals, lutein, zeaxanthin, or any other ingredient described hereinabove. The nutritional compositions described herein may be administered once per day or via several administrations throughout the course of a day.

Examples are provided to illustrate some embodiments of the nutritional composition of the present disclosure but should not be interpreted as any limitation thereon. Other embodiments within the scope of the claims herein will be apparent to one skilled in the art from the consideration of the specification or practice of the nutritional composition or methods disclosed herein. It is intended that the specification, together with the example, be considered to be exemplary only, with the scope and spirit of the disclosure being indicated by the claims which follow the example.

Example 1

This example illustrates an embodiment of a nutritional composition according to the present disclosure.

| Nutrient | per 100 kcal |
| --- | --- |
| Protein (g) | 3 |
| Fat (g) | 5.2 |
| Carbohydrates (g) | 10.5 |
| Polar lipids (mg) | 100 |
| Prebiotic (g) | 0.6 |
| Lactoferrin (mg) | 90 |

-continued

| Nutrient | per 100 kcal |
|---|---|
| DHA (mg) | 20 |
| ARA (mg) | 40 |
| Vitamin A (IU) | 1400 |
| Vitamin D (IU) | 300 |
| Vitamin E (IU) | 8 |
| Vitamin K (mcg) | 20 |
| Thiamin (mcg) | 300 |
| Riboflavin (mcg) | 350 |
| Vitamin B6 (mcg) | 225 |
| Vitamin B12 (mcg) | 0.5 |
| Niacin (mcg) | 5000 |
| Folic acid (mcg) | 60 |
| Panthothenic acid (mcg) | 2000 |
| Biotin (mcg) | 6 |
| Vitamin C (mg) | 50 |
| Choline (mg) | 22 |
| Calcium (mg) | 175 |
| Phosphorus (mg) | 100 |
| Sodium (mg) | 55 |
| Potassium (mg) | 125 |
| Chloride (mg) | 100 |
| Iodine (mcg) | 35 |
| Iron (mg) | 2.2 |
| Zinc (mg) | 1.7 |
| Manganese (mcg) | 12 |
| Copper (mcg) | 150 |
| Selenium (mcg) | 5 |
| Chromium (mcg) | 4 |
| Molybdenum (mcg) | 3 |
| Inositol (mg) | 50 |
| Carnitine (mg) | 3 |
| Taurine (mg) | 10 |
| Adenosine monophosphate (mg) | 0.8 |
| Cytidine monophosphate (mg) | 4 |
| Guanosine monophosphate (mg) | 0.5 |
| Uridine monophosphate (mg) | 1 |

Example 2

This example illustrates another embodiment of a nutritional composition according to the present disclosure.

| Nutrient | per 100 kcal |
|---|---|
| Protein (g) | 2 |
| Fat (g) | 5 |
| Carbohydrates (g) | 11 |
| Prebiotic (g) | 0.6 |
| Beta glucan (mg) | 9 |
| Polar lipids (mg) | 100 |
| Lactoferrin (mg) | 90 |
| Probiotic(s) (cfu) | $1 \times 10^8$ |
| DHA (mg) | 22 |
| ARA (mg) | 40 |
| Vitamin A (IU) | 400 |
| Vitamin D (IU) | 75 |
| Vitamin E (IU) | 2 |
| Vitamin K (mcg) | 12 |
| Thiamin (mcg) | 120 |
| Riboflavin (mcg) | 200 |
| Vitamin B6 (mcg) | 100 |
| Vitamin B12 (mcg) | 0.5 |
| Niacin (mcg) | 1100 |
| Folic acid (mcg) | 20 |
| Panthothenic acid (mcg) | 600 |
| Biotin (mcg) | 4 |
| Vitamin C (mg) | 18 |
| Choline (mg) | 30 |
| Calcium (mg) | 120 |
| Phosphorus (mg) | 60 |
| Sodium (mg) | 28 |
| Potassium (mg) | 140 |
| Chloride (mg) | 100 |

-continued

| Nutrient | per 100 kcal |
|---|---|
| Iodine (mcg) | 22 |
| Iron (mg) | 2 |
| Zinc (mg) | 1.2 |
| Manganese (mcg) | 25 |
| Copper (mcg) | 100 |
| Selenium (mcg) | 4 |
| Inositol (mg) | 8 |
| Carnitine (mg) | 3 |
| Taurine (mg) | 8 |
| Adenosine monophosphate (mg) | 1 |
| Cytidine monophosphate (mg) | 4 |
| Guanosine monophosphate (mg) | 0.8 |
| Uridine monophosphate (mg) | 1 |

Example 3

To study the effect of a blend of PDX and GOS on microbiota, neonatal piglets were randomized to receive either sow-milk replacer formula (Control (C), n=8) or sow-milk replacer formula supplemented with 2 g/L each GOS and PDX (G+P, n=9) for 19 days. Ileal (IL) and ascending colon (AC) contents were collected for further analysis for analysis of in depth analysis of the lactobacilli community by both culture-dependent (PCR) and culture-independent pyrosequencing methods.

Culture-Dependent Analysis:

Lactobacilli isolates were grown in 2 ml MRS to stationary phase. Following growth, bacterial genomic DNA was isolated using a modified bead-beating technique. For identification of lactobacilli, a partial HSP60 sequence was PCR amplified using lactobacilli specific HSP60 primers, LB308F (5'-TGAAGAAYGTNRYNGCYGG-3') and LB806RM (5'-AANGTNCCVCGVATCTTGTT-3'). PCR products were quantified using a NanoDrop ND-1000 Spectrophotometer (NanoDrop, Wilmington, Del.). Sanger sequencing was done with either primer (LB308F or LB806RM) using an ABI 3730XL capillary sequencers. The sequences were trimmed for quality and uploaded to the BLAST database (NCBI) to determine identity. Species identity was determined at 97% sequence similarity.

High-Throughput Pyrosequencing:

Bacterial genomic DNA was isolated from 200-300 mg of IL and AC contents using a modified bead beating method using QIAmp DNA Stool Kits (Qiagen, Valencia, Calif.). Extracted genomic DNA was quantified by NanoDrop and analyzed by pyrosequencing at the Research and Testing Laboratory (RTL, Lubbock, Tex.) based upon RTL protocols. Microbiota diversity and richness was quantified as the number of operational taxonomic units (OTUs) or with Chao1's richness estimator (OTUs and Chao1 were defined based on 3% divergence). Indicator species analysis was used to identify individual species within the genus *Lactobacillus* that were indicative of each of the diets. Indicator species analysis synthesizes information about occurrence and abundance of individual taxa, and this information is summarized as an indicator score. The analysis also provides a randomization test of the degree to which taxa are indicative of a particular state.

There were 13 species of *Lactobacillus* found in IL contents (FIG. 1(a)). Indicator species analysis showed *L. plantarum* and *L. amylovorous* to be indicative of the group Control (C) but not the GOS+PDX (G+P) group. *L. vaginalis, L. johnsonii* and *L. reuteri* were more indicative of the (G+P) group. Less lactobacilli diversity was observed in the AC by pyrosequencing, with only 6 different species detected (FIG. 1(b)). *L. johnsonii, L. mucosae, L. agilis* and *L. reuteri* were highly indicative of the G+P group as compared to the C group. Two species were slightly indicative of the C group, *L. vaginalis* and *L. rogosae*. Levels of *L. vaginalis, L. johnsonii* and *L. reuteri* in G+P group were similar to the levels of the sow-reared group.

Stress, sustained pain, or prolonged inflammation in the neonatal period may adversely affect development and subsequently lead to lower thresholds for pain in later life. Rat hyperalgesia was used as a model of post-inflammatory visceral pain sensitivity. Animals were fed either a control diet or a diet with PDX and GOS. The animals were kept on the diets through all behavioral testing conditions until study completion. Colitis was induced by intracolonic injection of zymosan in pups on postnatal day 14 producing short-term inflammation and subsequent long-term colonic hypersensitivity. On postnatal day 21 day, the pups were weaned from their respective mother and the measurements and samples were collected on postnatal day 60. The viscera-motor response (VMR) to colorectal distension (CRD) was quantified using electromyography (EMG) recordings from the external oblique muscle as an objective measure of visceral sensation.

FIG. 2 shows an effect of GOS/PDX diet on the viscera-motor response in neonatal rats with colitis. Neonatal injection with the inflammatory reagent (Zymosan) produced visceral hyperalgesia in adult rats as observed by significant increase in EMG of Control+Zymosan (red) compared to intra-colonic saline-treated rats (Control; blue). Treatment with GOS/PDX (green) significantly attenuated the viscera-motor response. This study has demonstrated that GOS/PDX mixture lowers the visceral hypersensitivity. Number of mice=19; asterisk indicates statistical significance at p<0.05.

Figure 3:
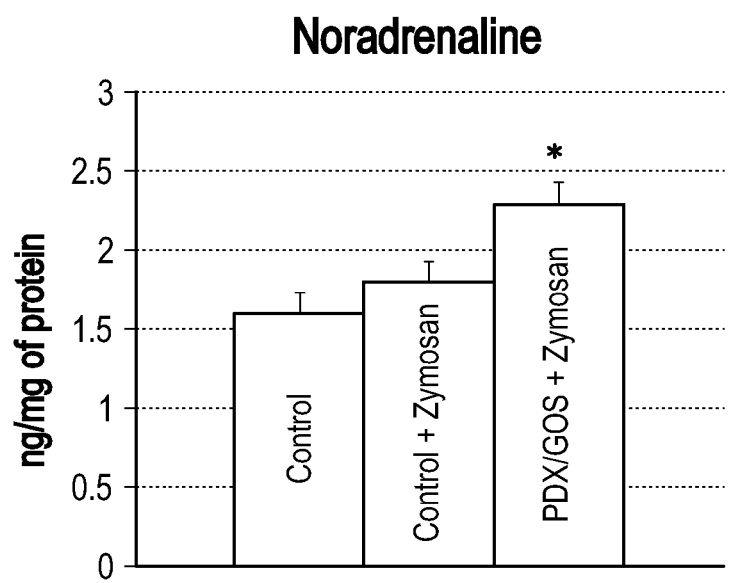
FIG. 3 is a graph that shows the increased level of noradrenaline in cerebellum following treatment with the GOS/PDX diet.

It has also been demonstrated that the GOS/PDX treatment affected the levels of brain neurotransmitters and amino acids. Neurotransmitters have an essential role in the development of the nervous system during infancy and childhood. The levels of most neurotransmitters are associated with synapse formation. FIG. 3 shows the increased level of noradrenaline in cerebellum following treatment with the GOS/PDX diet. This analysis used 5 mice per experimental group; asterisk indicates statistical significance at p<0.05.

Figure 4:
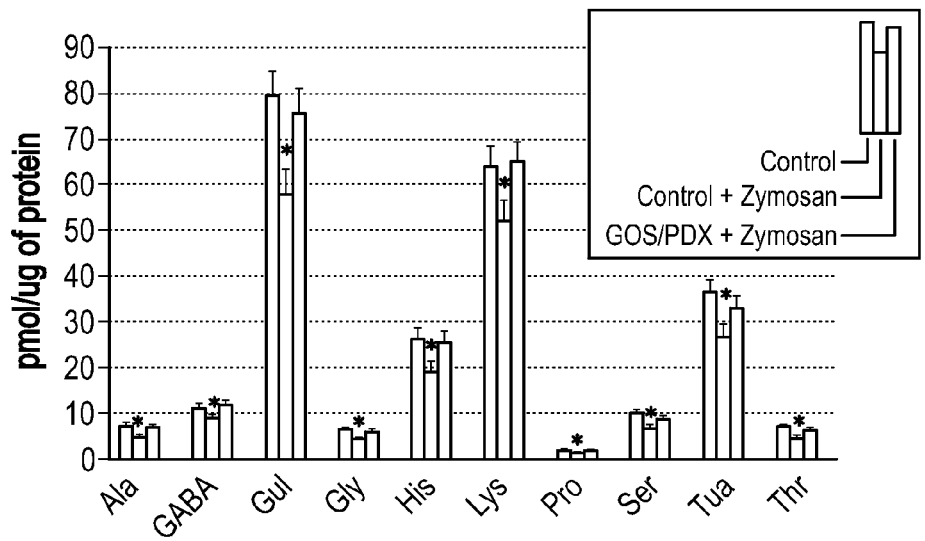
FIG. 4 is a graph that describes the effect of GOS/PDX on neurotransmitters and amino acids in the frontal cortex.

FIG. 4 describes the effect of GOS/PDX on neurotrasmitters and amino acids in the frontal cortex. The animals treated with GOS/PDX showed significant effect by bringing the levels of alanine, GABA, glutamine, glycine, histidine, lysine, proline, serine, taurine and threonine to the levels of non-zymosan animals. This analysis used 5 mice per experimental group; * indicates statistical significance at p<0.05.

Example 4

Full-term piglets were blocked by litter of origin and were randomly allotted to either sow-milk replacer formula with (COS+PDX, n=14) or without (Control, n=14) GOS+PDX. Pigs were fed ~60% ad libitum of sow-milk replacer formulas offered 3 times daily for 18 d to achieve growth rates similar to sow-fed pigs. At the end of the feeding, whole brains were obtained and stored at −80° C. Brain regions were dissected on a cryostat (−20° C.) using Harris Uni-Core micropunches and frozen immediately and later utilized for the analysis of the biogenic amine content at the Vanderbilt University Neurochemistry Core. Data were normalized to protein content within each sample. Means and standard errors were calculated and groups compared by unpaired Student's t-test.

Biogenic Amines/Neurotransmitters:

Biogenic amines (neurotransmitters) are determined by a specific HPLC assay. The following biogenic amines were detected noradrenaline, adrenaline, DOPAC, dopamine, 5-HIAA, HVA, 5-HT, and 3-MT.

Protein:

Total protein concentration of the brain extracts are determined using BCA Protein Assay Kit purchase from Pierce Chemical Company (Rockford, Ill.).

Figure 5:
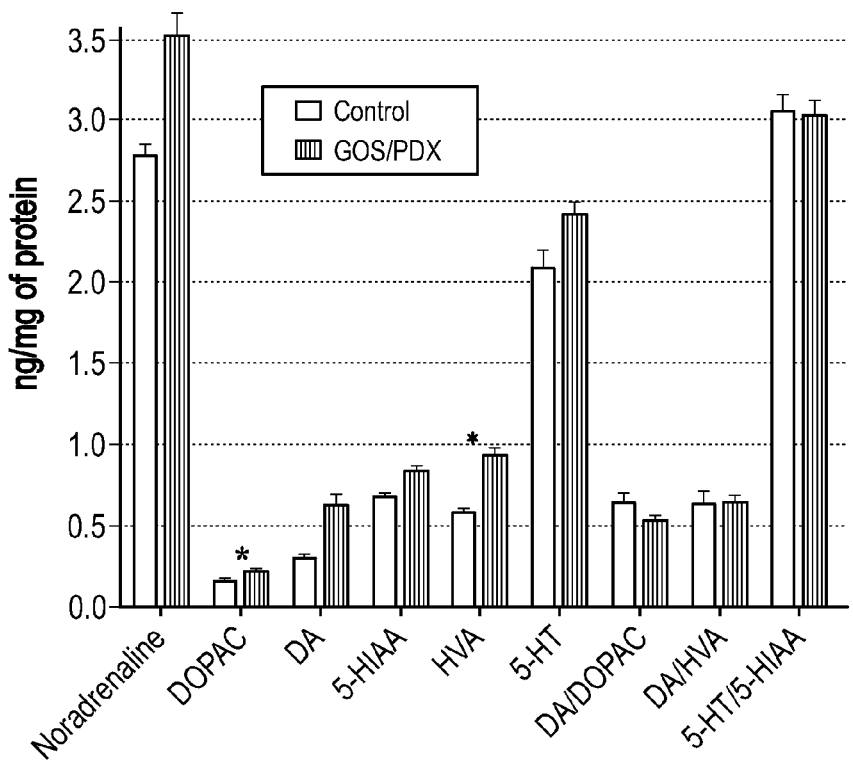
FIG. 5 is a graph that demonstrates that GOS+PDX feeding in neonate piglets modulates brain neurotransmitter content and metabolism.

FIG. 5 demonstrates that GOS+PDX feeding in neonate piglets modulates brain neurotransmitter content and metabolism both of which may be reflective of enhanced neural transmission within the developing frontal cortex.

Example 5

Rodents were fed either a control diet (AIN93-G based) or a diet with PDX and GOS added to approximate a dosage that is similar to that received by infants consuming our infant formula with 2 g/L of PDX and 2 g/L of GOS. The diets were fed to the rodents starting just after weaning from the dam (postnatal day 21-23) for at least 28 days prior to behavioral testing. The animals were kept on the diets through all behavioral testing conditions until study completion.

Figure 6:
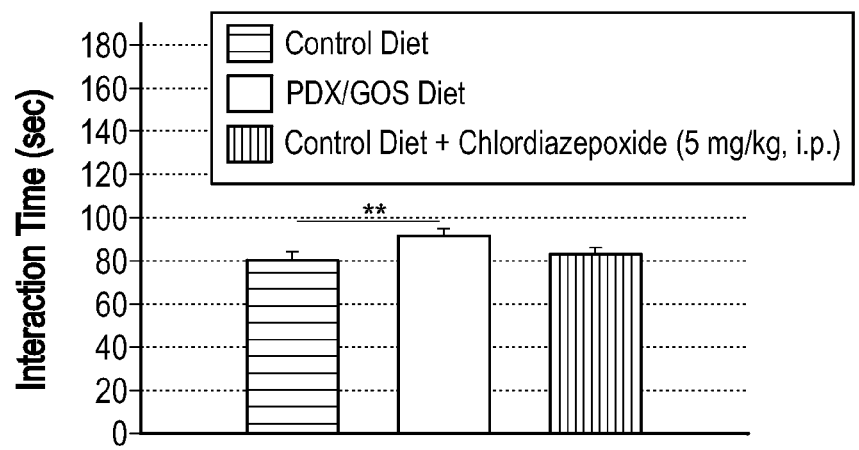
FIG. 6 is a graph illustrating the results of a social interaction test using Sprague-Dawley rats.

The results of a social interaction test using Sprague-Dawley rats and included a pharmacological control that was expected to impact social interactions are shown in FIG. 6. In brief, the experimental rat was exposed to a new rat it had never encountered before, and specific behaviors defined as positive social interactions were counted by a trained observer over a 6 minute period. Examples of social interaction include sniffing, grooming, climbing, following or ano-genital exploration. Aggressive or incidental interactions were not included in the test. It is therefore interpreted that feeding young rats dietary PDX and GOS significantly improves their social interactions.

Figure 7:
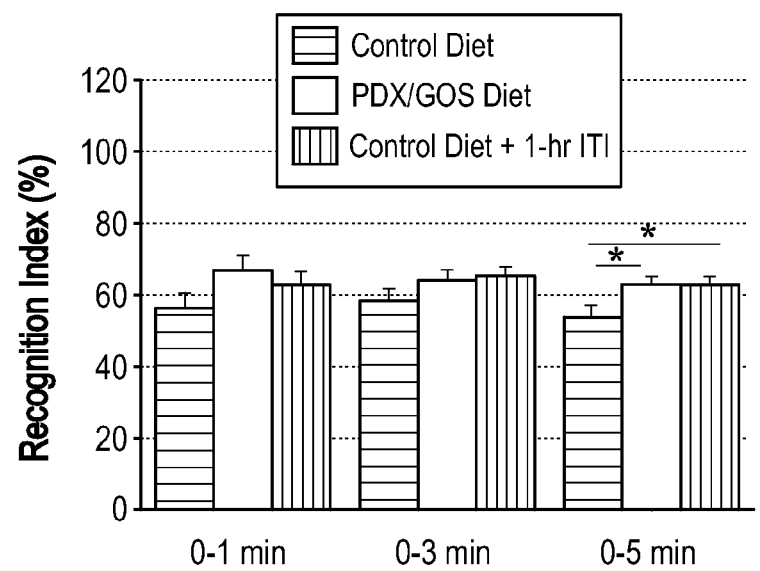
FIG. 7 is a graph that shows the results of a novel object recognition test using Long Evans rats to measure episodic memory including a 1 hour time-point as a positive control.

The results of a novel object recognition test using Long Evans rats to measure episodic memory including a 1 hour time-point as a positive control are shown in FIG. 7. For this test, rats are familiarized to an open-field arena during a 5 minute habituation period on days 1 and 2 of the test. Training begins on day 3 where two identical objects are placed into the arena prior to allowing the rat to explore the arena for 3 minutes. The rat is put back in its home cage for 48 h and is then brought back to the same arena containing one original object and 1 new object where the time spent investigating is recorded over 5 minutes. All rodents have a strong preference to explore new things. So, if a rat has memory for the original object, this is revealed by observing the rat explore the new object more than the original object. This difference is expressed as the recognition index, and the data below clearly reveal that rats fed PDX and GOS displayed an increased recognition index, suggesting they had improved episodic memory compared to control fed rats. The rats that were brought back to the arena after just 1 hour also show increased recognition index, validating the model.

Figure 8:
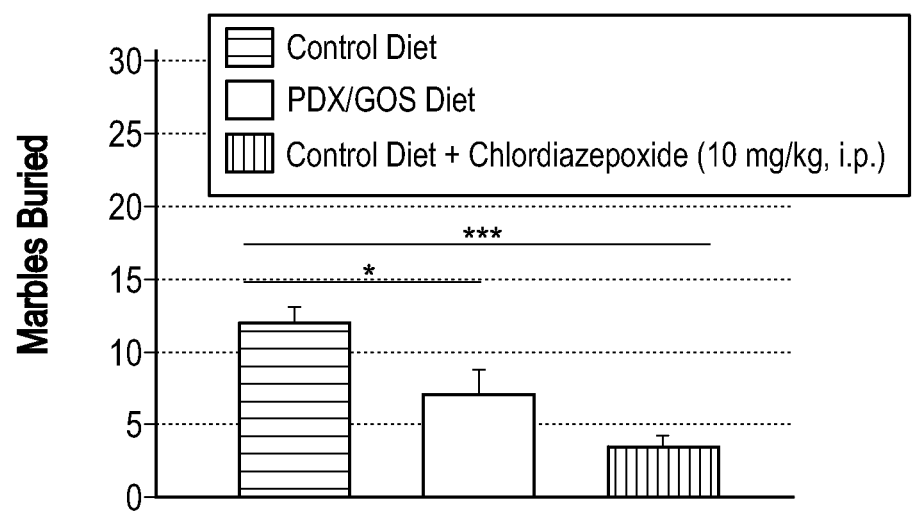
FIG. 8 illustrates the results of a marble burying test using C57/bl6 mice used to measure anxiety and obsessive compulsive tendencies.

The results of a marble burying test using C57/bl6 mice used to measure anxiety and obsessive compulsive tendencies are shown in FIG. 8. It is well established that mice will attempt to bury new objects in their environment. Drugs used to treat anxiety are known to reduce the intensity of this behavior in mice. For this test, an individual mouse is placed into a new cage containing 20 black glass marbles arranged in a grid of 5 rows and observed for 30 minutes. The number of marbles buried is counted, as well as video recording analysis to measure total activity. The data revealed that mice fed PDX and GOS buried fewer marbles than control diet fed mice, suggesting they were less anxious about their environment in this test.

Example 6

A Visual Water-Y-Maze Task (VWT) is conducted in a water tank that is narrower on one end and wider on the other, with the wider end divided into a left and right compartment by a partition. One compartment is illuminated and contains a transparent escape platform at the end; the other is dark and does not lead to escape. The left-right location of the platform switches randomly, but its true location is always signaled by the light-dark contrast. In order to expedite its escape from the water, the animal must learn to make its decision to swim left or right based on this visual cue. Two sessions were conducted across two consecutive days, each session consisting of 30 trials spaced apart by ~3 min intervals. For this study rats were fed 3 different levels of bovine lactoferrin, 500 mg, 1000 mg, and 2000 mg/kg bodyweight.

Figure 9A:
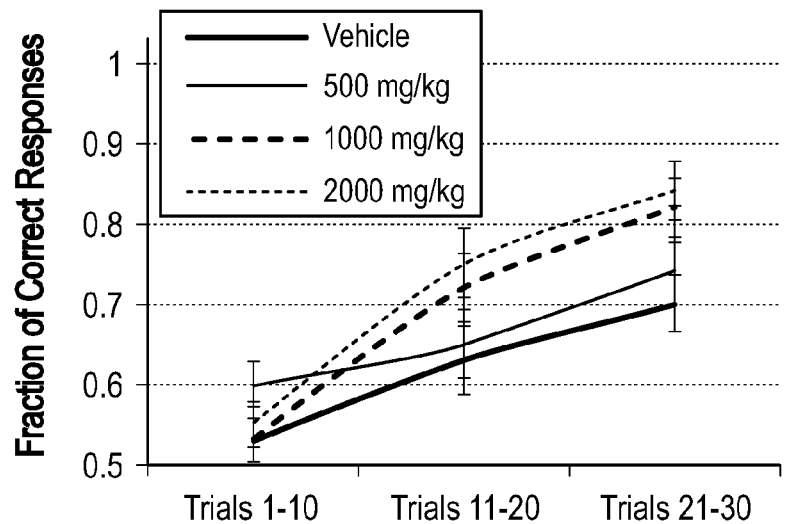
FIG. 9a provides learning curves for the first session were analyzed with a 3×5×4 (Trial×Litter×Dose) repeated measures ANOVA, with Trial serving as the repeated measure of the fraction of correct responses during the first 10, middle 10, and last 10 trials of the 30-trial session.
Figure 9B:
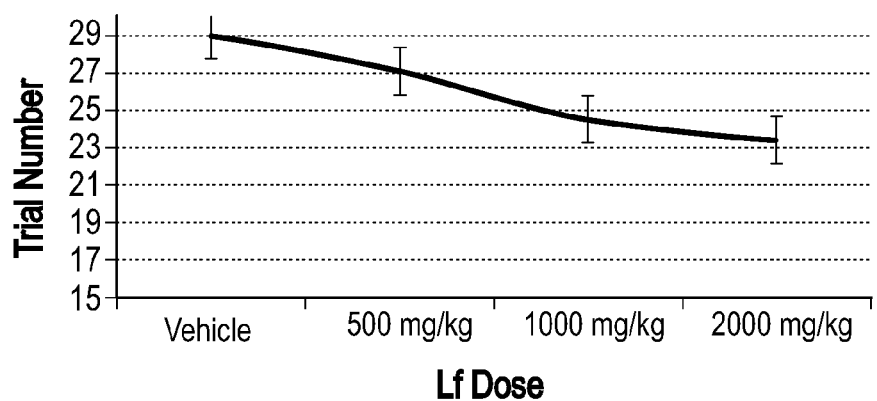
FIG. 9b shows the first-session acquisition data was analyzed using a more stringent trials-to-mastery criterion, defined as the first trial number at which 9 out of the 10 previous trials were performed correctly.

Learning curves for the first session were analyzed with a 3×5×4 (Trial×Litter×Dose) repeated measures ANOVA, with Trial serving as the repeated measure of the fraction of correct responses during the first 10, middle 10, and last 10 trials of the 30-trial session. A significant linear two-way (Trials×Dose) interaction was found, $F(4,20)=3.41$, $p=0.04$, indicating a linear dose-dependent increase in the slopes of the learning curves (FIG. 9a). Dunnett post hoc tests determined that both the 1000 and 2000 mg/kg group performed significantly better than vehicle in the last 10 trials ($p<0.05$).

The first-session acquisition data was analyzed using a more stringent trials-to-mastery criterion, defined as the first trial number at which 9 out of the 10 previous trials were performed correctly. Remarkably, only 20% of vehicle controls and 30% of the 500 mg/kg group achieved this criterion by the end of the first session whereas 70% of both the 1000 and 2000 mg/kg lactoferrin groups did. We analyzed these data with a 5×4 (Litter×Dose) univariate ANOVA, with subjects that failed to achieve mastery assigned a maximum score of 30 trials. Lactoferrin supplementation produced a significant linear dose-response curve, $p<0.003$). Dunnett post hoc tests confirmed that both the 1000 and 2000 mg/kg groups took significantly fewer trials than vehicle to master the visual discrimination ($p<0.05$).

Example 7

Holtzman rat pups were randomly assigned to treated and untreated groups. Daily lactoferrin supplementation began when the pups' eyes opened (at P16) and continued for 7 days before weaning (at P23) and 11 days after weaning (until P34), for a total of 18 days of supplementation during the peri-weaning critical period. The daily intake was based on infant intakes and resulted in 743 mg/kg bodyweight for rats.

Behavioral Testing, Escape Test.

Another test assessing active coping ability under aversive conditions, a shuttle box escape test, was conducted on the day following the last day of the forced swim test (P44, cohort 1; P47, cohort 2). The shuttle box test, which has been used previously to assess susceptibility to a depressive phenotype in the Holtzman rat, involves the delivery of a footshock which may be escaped by the subject performing crossings to the other side of the chamber. While this test usually consists of at least one session of inescapable shock before shuttle box testing, in this case, the previous two days of forced swim could be considered inescapable stress, which is perhaps sufficient to induce helpless behavior without the need for prior inescapable footshock.

The shuttle box (Med Associates; 42 cm×16 cm×25 cm) consisted of two compartments of equal size, separated by a door (11 cm×9 cm) that remained open throughout the session. The chamber was enclosed in a sound-attenuated box and illuminated by a white light. Two sides of the chamber were aluminum, with clear plexiglass for the front, back, and top. Footshocks (0.7 mA) were delivered through metal bars separated by 1.2 cm forming the floor of the chamber, which was wired to shock generators. The subject's position was detected by eight sets of infrared light beam motion detectors, located 2 cm above the grid floor, spaced 4.4 cm apart from each other, on both sides of the chamber. The computer program used beam breaks of the two pairs of beams located at either end of both sides of the chamber as the contingency for terminating shock, to score a complete crossing. The protocol consisted of 1 minute of habituation to the context, followed by 15 trials of fixed-ratio 1 contingency (FR1: one crossing to terminate shock; maximum trial length=15 sec), followed by 15 trials of fixed-ratio 2 (FR2: two crossings, back and forth, to terminate shock; maximum trial length=30 sec). Intertrial intervals varied pseudorandomly between 10-60 seconds; the average session length was 26 minutes. A trial was considered a "success" if the footshock was terminated by a sufficient number of crossings prior to the trial timing out.

Figure 10:
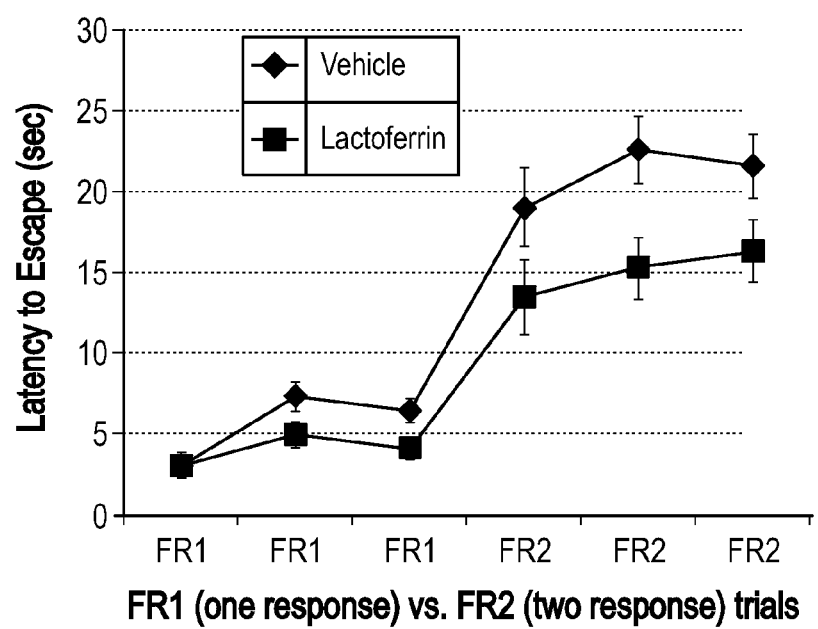
FIG. 10 illustrates how lactoferrin subjects showed superior performance in an aversively motivated task, showing significantly shorter latencies to escape an aversive footshock, $F(1,22)=4.7$, $p=0.04$. The difference was especially salient when escape was made difficult (by requiring a sequence of two responses instead of one).

Oral administration of nutritional doses of bovine lactoferrin, when given during the period around weaning (in this case, daily administrations beginning 1 week before weaning and continuing 1.5 weeks after weaning) improved learning of an active coping strategy in response to a stressor, with the results shown in FIG. 10.

All references cited in this specification, including without limitation, all papers, publications, patents, patent applications, presentations, texts, reports, manuscripts, brochures, books, internet postings, journal articles, periodicals, and the like, are hereby incorporated by reference into this specification in their entireties. The discussion of the references herein is intended merely to summarize the assertions made by their authors and no admission is made that any reference constitutes prior art. Applicants reserve the right to challenge the accuracy and pertinence of the cited references.

Although embodiments of the disclosure have been described using specific terms, devices, and methods, such description is for illustrative purposes only. The words used are words of description rather than of limitation. It is to be understood that changes and variations may be made by those of ordinary skill in the art without departing from the spirit or the scope of the present disclosure, which is set forth in the following claims. In addition, it should be understood that aspects of the various embodiments may be interchanged in whole or in part. For example, while methods for the production of a commercially sterile liquid nutritional supplement made according to those methods have been exemplified, other uses are contemplated. Therefore, the spirit and scope of the appended claims should not be limited to the description of the versions contained therein.

What is claimed is:

1. A method for enhancing brain development in a pediatric subject, the method comprising administering to the pediatric subject a nutritional composition comprising:
   a. up to about 7 g/100 kcal of a fat or lipid source, wherein the fat or lipid source comprises at least about 0.5 mg/100 kcal polar lipids, wherein the polar lipids comprise gangliosides and phospholipids, and further wherein the gangliosides are present at a level of about 0.5 mg/100 kcal to about 18 mg/100 kcal, and the phospholipids are present at a level of about 20 mg/100 kcal to about 250 mg/100 kcal;
   b. up to about 5 g/100 kcal of a protein source;
   c. at least about 15 mg/100 kcal of lactoferrin from a non-human source;
   d. a prebiotic composition, wherein at least 20% of the prebiotic composition comprises polydextrose, galactooligosaccharide or a combination thereof;
   e. at least about 5 mg/100 kcal of a source of long chain polyunsaturated fatty acids comprising docosahexaenoic acid; and
   f. a preservative.

2. The method of claim 1, wherein the polar lipids are present at a level of about 0.5 mg/100 kcal to about 470 mg/100 kcal.

3. The method of claim 2, wherein the polar lipids are present at a level of about 10 mg/100 kcal to about 350 mg/100 kcal.

4. The method of claim 3, wherein the polar lipids are present at a level of about 20 mg/100 kcal to about 260 mg/100 kcal.

5. The method of claim 1, wherein lactoferrin is present at a level of about 10 mg/100 kcal to about 200 mg/100 kcal.

6. The method of claim 5, wherein the lactoferrin is bovine lactoferrin.

7. The method of claim 1, wherein the source of long chain polyunsaturated fatty acids is present more preferably from about 5 mg/100 kcal to about 75 mg/100 kcal.

8. The method of claim 1, wherein the nutritional composition is an infant formula or a growing up milk.

9. A nutritional composition for enhancing brain development in a pediatric subject, comprising:
   a. up to about 7 g/100 kcal of a fat or lipid source, wherein the fat or lipid source comprises at least about 0.5 mg/100 kcal polar lipids, wherein the polar lipids comprise gangliosides and phospholipids, and further wherein the gangliosides are present at a level of about 0.5 mg/100 kcal to about 18 mg/100 kcal, and the phospholipids are present at a level of about 20 mg/100 kcal to about 250 mg/100 kcal;
   b. up to about 5 g/100 kcal of a protein source;
   c. at least about 15 mg/100 kcal of lactoferrin from a non-human source;
   d. a prebiotic composition, wherein at least 20% of the prebiotic composition comprises polydextrose, galactooligosaccharide or a combination thereof;
   e. at least about 5 mg/100 kcal of a source of long chain polyunsaturated fatty acids comprising docosahexaenoic acid; and
   f. a preservative.

10. The composition of claim 9, wherein the polar lipids are present at a level of about 0.5 mg/100 kcal to about 470 mg/100 kcal.

11. The composition of claim 10, wherein the polar lipids are present at a level of about 10 mg/100 kcal to about 350 mg/100 kcal.

12. The composition of claim 11, wherein the polar lipids are present at a level of about 20 mg/100 kcal to about 260 mg/100 kcal.

13. The composition of claim 9, wherein lactoferrin is present at a level of about 15 mg/100 kcal to about 300 mg/100 kcal.

14. The composition of claim 13, wherein the lactoferrin is bovine lactoferrin.

15. The composition of claim 9, wherein the source of long chain polyunsaturated fatty acids is present more preferably from about 5 mg/100 kcal to about 75 mg/100 kcal.

16. The composition of claim 9, wherein the nutritional composition is an infant formula or a growing up milk.

17. The method of claim 1, wherein the prebiotic composition is present in the nutritional composition from about 1.0 g/L to about 10.0 g/L.

18. The composition of claim 9, wherein the prebiotic composition is present from about 1.0 g/L to about 10.0 g/L.

19. The method of claim 1, wherein the pediatric subject is an infant and further wherein the gangliosides are present at a level of about 0.5 mg/100 kcal to about 12 mg/100 kcal and the phospholipids are present at a level of about 20 mg/100 kcal to about 50 mg/100 kcal.

20. The method of claim 1, wherein the pediatric subject is an infant between birth and 6 months of age, and further wherein the gangliosides are present at a level of about 0.5 mg/100 kcal to about 9 mg/100 kcal and the phospholipids are present at a level of about 20 mg/100 kcal to about 150 mg/100 kcal.

* * * * *